(12) United States Patent
Zeikus et al.

(10) Patent No.: US 6,495,023 B1
(45) Date of Patent: Dec. 17, 2002

(54) ELECTROCHEMICAL METHODS FOR GENERATION OF A BIOLOGICAL PROTON MOTIVE FORCE AND PYRIDINE NUCLEOTIDE COFACTOR REGENERATION

(75) Inventors: Gregory J. Zeikus, Okemos, MI (US); Hyoun S. Shin, Lansing, MI (US); Mahendra K. Jain, Lexington, KY (US)

(73) Assignee: Michigan State University, East Lansing, MI (US)

( * ) Notice: Subject to any disclaimer, the term of this patent is extended or adjusted under 35 U.S.C. 154(b) by 0 days.

(21) Appl. No.: 09/793,025

(22) Filed: Feb. 26, 2001

Related U.S. Application Data

(63) Continuation-in-part of application No. 09/350,072, filed on Jul. 8, 1999, now Pat. No. 6,270,649.
(60) Provisional application No. 60/092,190, filed on Jul. 9, 1998, provisional application No. 60/092,191, filed on Jul. 9, 1998, and provisional application No. 60/184,815, filed on Feb. 25, 2000.

(51) Int. Cl.$^7$ .................................................. C25B 3/00
(52) U.S. Cl. ....................... 205/413; 205/440; 205/450
(58) Field of Search ................................. 205/413, 440, 205/450, 424; 429/2, 43

(56) References Cited

U.S. PATENT DOCUMENTS 6,270,649 B1 * 8/2001 Zeikus et al. ............... 205/413

OTHER PUBLICATIONS

Mellor et al., "Reduction of Nitrate and Nitrite in Water by Immobilization Enzymes", Nature, vol. 355, pp. 717–719, Feb. 20, 1992.*
Hongo et al., "Application of Electro–Energizing Method of L–Glutamic Acid Fermentation", Agric. Biol. Chem., vol. 43, No. 10, pp. 2075–2081, no month available, 1979.*

* cited by examiner

Primary Examiner—Edna Wong
(74) Attorney, Agent, or Firm—Quarles & Brady LLP

(57) ABSTRACT

Disclosed are methods using neutral red to mediate the interconversion of chemical and electrical energy. Electrically reduced neutral red has been found to promote cell growth and formation of reduced products by reversibly increasing the ratio of the reduced:oxidized forms of NAD(H) or NADP(H). Electrically reduced neutral red is able to serve as the sole source of reducing power for microbial, cell growth. Neutral red is also able to promote conversion of chemical energy to electrical energy by facilitating the transfer of electrons from microbial reducing power to a fuel cell cathode.

18 Claims, 10 Drawing Sheets

ELECTROCHEMICAL METHODS FOR GENERATION OF A BIOLOGICAL PROTON MOTIVE FORCE AND PYRIDINE NUCLEOTIDE COFACTOR REGENERATION

CROSS-REFERENCE TO RELATED APPLICATIONS

This application is a continuation-in-part of U.S. Ser. No. 09/350,072, filed Jul. 8, 1999, now U.S. Pat. No. 6,270,649 which claims benefit to U.S. Provisionals Ser. No. 60/092,190 and Ser. No. 60/092,191, both filed Jul. 9 1998. This application also claims the benefit of U.S. Provisional Ser. No. 60/184,815 filed Feb. 25, 2000. These applications are incorporated by reference herein.

STATEMENT REGARDING FEDERALLY SPONSORED RESEARCH OR DEVELOPMENT

This invention was made with U.S. Government support in the form of the United States Department of Energy grant DE-FG02-93ER20108. The United States may have certain rights in this invention.

BACKGROUND OF THE INVENTION

Microbial fermentation and biotransformation reactions are being employed with increasing frequency in the production of a number of commercially and industrially important products. There is also growing interest in developing alternative energy sources through microbial fermentation of waste materials. The economic feasibility of these processes depends on maximizing the efficiency of the fermentation or biotransformation reactions.

Bacterial species are able to use various energy sources, including light and diverse organic and inorganic chemicals, for growth and metabolism. These energy sources are used to produce an electrochemical gradient that provides an electron donor for metabolism and allows maintenance of a membrane potential and proton motive force. The energetics of living systems are driven by electron transfer processes in which electrons are transferred from a substrate, which is thereby oxidized, to a final electron acceptor, which is thereby reduced.

In microbial metabolism, the energy produced from the driving force of electrons is directly proportional to the potential energy difference ($\Delta E_0'$) between the initial electron donor (the first biochemical dehydrogenating reaction) and final electron acceptor (e.g., the final biochemical hydrogenating reaction).

Certain microorganisms (e.g., Escherichia and Actinobacillus) are able to grow using $H_2$ as an electron donor to reduce fumarate into succinate in an anaerobic respiration process. These bacteria obtain free energy and reducing power from the electron driving force generated by the $E_0'$ difference between the coupled oxidoreduction half reactions of [$2H^+/H_2$] and [fumarate/succinate].

Methanogens are strict anaerobic archea that can couple $H_2$ or HCOOH oxidation to $CO_2$ reduction into methane. Methanogenesis produces less free energy than other anaerobic respiration processes (e.g., fumarate, nitrate, or sulfate reduction) because the $E_0'$ difference between the half oxidation reduction reactions of [$2H^+/H_2$] and [$CO_2/CH_4$] is relatively small.

Hydrogen oxidation by microbial hydrogenases can be coupled to reduction of various biological electron carriers including $NAD^+$, cytochromes, and quinones or to certain artificial redox dyes, such as methyl-viologen and neutral red (NR) (Annous, et al., 1996, *Appl. Microbiol. Biotechnol.* 45:804–810, Kim, et al., 1992, *J. Microbiol. Biotechnol.* 2:248–254). The effect of redox dyes, with or without electrochemical reduction systems, on metabolite patterns and $H_2$ production has been examined in several microbial processes, including the glutamate (Hongo, et al., 1979, *Agric. Biol. Chem.* 43:2083–2986), butanol (Girbal, et al., 1995, *Microbiol. Rev.* 16:151–162 and Kim, et al., 1992, *J. Microbiol. Biotechnol*, 2:268–272), and butyrate (Shen, et al., 1996, *Appl. Microbiol, Biotechnol*, 45:355–362) fermentations.

The specific activities of redox enzymes involved in bacterial catabolism, such as hydrogenase or fumarate reductase, can be measured using their in vivo electron carriers (e.g., NAD or menanquinone) or with artificial redox dyes (e.g., benzyl viologen) (Cecchini, et al., 1986, *Proc. Natl. Acad. Sci. USA* 83:8898–8902, Dickie, et al., 1979, *Can. J. Biochem.*, 57:813–821, Kemner, et al., 1994, *Arch. Microbiol.*, 161:47–54, Petrov, et al., 1989, *Arch. Biochem. Bio-phys.* 268:306–313, and Wissenbach, et al., 1990, *Arch. Microbiol.* 154:60–66). Bacteria that produce succinic acid as a major catabolic end product (e.g., *E. coli, Wolinella succinogenes* and other species) have a fumarate reductase (FRD) complex that catalyzes fumarate-dependent oxidation of menaquinone. This reaction is coupled to the generation of a transmembrane proton gradient that is used by the organism to support growth and metabolic function (Kortner, et al., 1992, *Mol. Microbiol.* 4:855–860 and Wissenbach, et al., 1992, *Arch. Microbiol.* 158:68–73). The fumarate reductase of *E. coli* is composed of four nonidentical subunits: FRDA, FRDB, FRDC, and FRDD. The subunits are arranged in two domains: (i) the FRDAB catalytic domain and the FRDCD membrane anchor domain, which is essential for electron transfer and proton translocation reactions involving menaquinone (Cecchini, et al., 1995, *J. Bacteriol.* 177:4587–4592, Dickie, et al., 1979, *Can. J. Biochem.*, 57:813–821, and Westenberg, et al., 1990, *J. Biol. Chem.* 265:19560–19567). Subunits FRDA and FRDB retain catalytic activity in solubilized membrane preparations.

Electrochemical techniques employing redox dyes are useful for investigating the oxidation-reduction characteristics of biological systems and provide information about biological energy metabolism (Moreno, et al., 1993, *Eur. J. Biochem.* 212:79–86 and Sucheta, et al., 1993, *Biochemistry* 32:5455–5465). Redox dyes that are useful in bioelectrochemical systems must easily react with both the electrode and the biological electron carriers. Many biological electron carriers, such as NAD (Miyawaki, et al., 1992, *Enzyme Microb. Technol.* 14:474–478 and Surya, et al., 1994, *Bioelectrochem. Bioenerg.* 33:71–73), c-type cytochromes (Xie, et al., 1992, *Bioelectrochem. Bioenerg.* 29:71–79), quinones (Sanchez, et al., 1995, *Bioelectrochem. Bioenerg.* 36:67–71), and redox enzymes, such as nitrite reductase (White, et al., 1987, *Bioelectro-chem. Bioenerg.* 26:173–179), nitrate reductase (Willner, et al., 1992, *Bioelectrochem. Bioenerg.* 29:29–45), fumarate reductase (Sucheta, et al., 1993, *Biochemistry.* 32:5455–5465), glucose-6-phosphate dehydrogenase (Miyawaki, et al., 1992, *Enzyme Microb. Technol.* 14:474–478), ferredoxin-NADP reductase (Kim, et al., 1992, *J. Microbiol. Biotechnol.* 2:2771–2776) and hydrogenase (Schlereth, et al., 1992, *Bioelectrochem. Bioenerg.* 28:473–482) react electrochemically with the redox dyes.

Certain redox dyes with lower redox potentials than that of NAD, such as methyl viologen (MV) (Kim, et al., 1988, *Biotechnol. Lett.* 10:123–128, Pequin, et al., 1994, *Biotech-* nol. Lett. 16:269–274, and White, et al., 1987, FEMS Microbiol. Lett. 43:173–176), benzyl viologen (Emde, et al., 1990, Appl. Environ. Microbiol. 56:2771–2776), and neutral red (NR) (Girbal, et al., 1995, FEMS Microbiol. Rev. 16:151–162 and Kim, et al., J. Biotechnol. 59:213–220) have been correlated with alterations in the rate of biological redox reactions in vivo. Hongo and Iwahara (Hongo, et al., 1979, Agric. Biol. Chem. 43A:2075–2081 and Hongo, et al., 1979, Agric. Biol. Chem. 43B:2083–2086) discovered that including redox dyes with low $\Delta E_0'$ values (e.g., MV, benzyl viologen and NR) in bacterial fermentation conducted under cathodic reduction conditions was correlated with an increase in L-glutamate yield (about 6%). In the method of Hongo and Iwahara, a platinum electrode was used to deliver electricity at a level that was sufficiently high to generate hydrogen from water. Therefore, the source of increased reducing power in the method of Hongo and Iwahara is not known, nor was the mechanism by which the tested dyes affect fermentation characterized. Addition of NR to acetone-butanol fermentations is correlated with decreased production of acids and $H_2$, and enhanced production of solvent (Girbal, et al., 1995, FEMS Microbiol. Rev. 16:151–162 and Kim, et al., 1992, J. Microbiol. Biotechnol. 2:2771–2776), an effect that was further enhanced under electroenergized fermentation conditions (Ghosh, et al., 1987, abstr. 79. In Abstracts of Papers, 194th ACS National Meeting. American Chemical Society). Viologen dyes have been used as electron mediators for many electrochemical catalytic systems using oxidoreductases in vitro and in vivo (James, et al., 1988, Electrochem. Bioenerg. 20:21–32, Kim, et al., 1988, Biotechnol. Lett. 10:123–128, Moreno, et al., 1993, Eur. J. Biochem. 212:79–86, Schlereth, et al., 1992, Bioelectrochem. Bioenerg. 28:473–482, and White, et al., 1987, FEMS Microbiol. Lett. 43:173–173).

An electrochemical system was used to regenerate reduced iron for growth of Thiobacillus ferrooxidans on electrical reducing power (Robinson, et al., 1982, Can. J. Biochem. 60:811–816).

It may be possible to control or alter metabolism by linking biochemical processes to an external electrochemical system. Linking biochemical and electrochemical systems may allow the use of electricity as a source of electrons for bacterial growth and in vivo or in vitro fermentation or biotransformation reactions.

A reversible biochemical-electrochemical link may allow conversion of microbial metabolic or enzyme catalytic energy into electricity. Biofuel cells in which microbial energy is directly converted to electrical energy using conventional electrochemical technology have been described (Roller, et al., 1984, J. Chem. Tech. Biotechnol. 34B:3–12 and Allen, et al., 1993, Appl. Biochem. Biotechnol. 39–40:27–40). Chemical energy can be converted to electric energy by coupling the biocatalytic oxidation of organic or inorganic compounds to the chemical reduction of the oxidant at the interface between the anode and cathode (Willner, et al., 1998, Bioelectrochem. Bioenerg. 44:209–214). However, direct electron transfer from microbial cells to electrodes has been shown to take place only at very low efficiency (Allen, et al., 1972, J. R. Norris and D. W. Ribbons (eds.), Academic Press, New York, 6B:247–283).

The electron transfer efficiency can be improved by using suitable redox mediators (Bennetto, et al., 1985, Biotechnol. Lett. 7:699–105), and most of the microbial fuel cells studied employed electron mediators such as the redox dye thionin (Thurston, et al., 1985, J. Gen. Microbiol. 131:1393–1401). In microbial fuel cells, two redox couples are required for: (1) coupling the reduction of an electron mediator to bacterial oxidative metabolism; and (2) coupling the oxidation of the electron mediator to the reduction of the electron acceptor on the cathode surface (where the electron acceptor is regenerated by atmospheric oxygen) (Ardeleanu, et al., 1983, Bioelectrochem. Bioenerg. 11:273–277 and Dealney, et al., 1984, Chem. Tech. Biotechnol. 34B:13–27).

The free energy produced by either normal microbial metabolism or by microbial fuel cell systems is mainly determined by the potential difference ($\Delta E_0'$) between the electron donor and acceptor according to the equation, $-\Delta G = nF\Delta E_0$ in which $\Delta G$ is the variation in free energy, n is the number of electron moles, and F is the Faraday constant (96,487 J/volt) (Dealney, et al., 1984, Chem. Tech. Biotechnol. 34B:13–27). Coupling of the metabolic oxidation of the primary electron donor (NADH) to the reduction of the final electron acceptor (such as oxygen or fumarate in bacterial respiration systems) is very similar to the coupling of electrochemical half-reaction of the reductant (electron donor) to the half reaction of the oxidant (electron acceptor) in a fuel cell or battery system (Chang, et al., 1981, 2nd ed., Macmillan Publishing, New York). Biological reducing power sources such as NADH ($E_0'=-0.32$ volt), $FdH_2$ ($E_0'=-0.42$ volt), or $FADH_2$ ($E_0'=-0.19$ volt) with low redox potentials can act as reductants for fuel cells, but they are not easily converted to electricity because the cytoplasmic membrane must be non-conductive to maintain the membrane potential absolutely required for free energy (i.e., ATP) production (Thauer, et al., 1997, Bacteriol. Rev. 41:100–180).

For electron transfer to occur from a microbial electron carrier to an electrode, an electron mediator is required (Fultz, et al., 1982, Anal. Chim. Acta. 140:1–18). Allen, et al. (1993, Appl. Biochem. Biotechnol. 39–40:27–40) reported that the reducing power metabolically produced by Proteus vulgaris or E. coli can be converted to electricity by using electron mediators such as thionin. Tanaka, et al. (1985, Chem. Tech. Biotechnol. 35B:191–197 and 1988, Chem. Tech. Biotechnol. 42:235–240) reported that light energy can be converted to electricity by Anabaena variabilis using HNQ as the electron mediator. Park, et al. (1997, Biotech. Techniq. 11:145–148) confirmed that viologen dye crosslinked with carbon polymers and adsorbed to Desulfovibro desulfuricans cytoplasmic membranes can mediate electron transfer from bacterial cells to electrodes or from electrodes to bacterial cells.

There remains a need in the art for improved, more efficient methods for converting metabolic reducing power to electrical energy, and for converting electrical energy to metabolic reducing power.

BRIEF SUMMARY OF THE INVENTION

One aspect of the present invention is a method of promoting reductive processes in a bioreactor system comprising the steps of (a) providing an electrochemical bioreactor system having a cathode compartment equipped with a cathode and an anode compartment equipped with an anode, the cathode and anode compartment being separated by a cation selective membrane, wherein the cathode and anode are connected by a conductive material to a power supply; (b) placing a suitable amount of neutral red and a biological catalyst in the cathode compartment.

In a particularly advantageous form of the invention, the biological catalyst is an enzyme that uses NADH or NADPH as a cofactor. The cathode compartment comprises NADH or NADPH and an oxidized substrate for the enzyme. Electrically reduced neutral red transfers electrons to $NAD^{30}$ or NADP$^{30}$. In a preferred form of the invention, the enzyme is oxidoreductase, most particularly in alcohol dehydrogenase, the oxidized substrate is an aldehyde or ketone and the reduced product is an alcohol.

Another aspect of the invention is a method for generating electricity using a biological system comprising the steps of (a) providing an electrochemical fuel cell system comprising an anode compartment and a cathode compartment separated by a cation-selective membrane, wherein each compartment is equipped with an electrode, wherein the electrodes are connected by a wire to a multimeter; (b) placing an anolyte in the anode compartment, the anolyte comprising a suitable concentration of neutral red and a biological catalyst selected from the group consisting of bacteria, archea, plant cells, and animal cells; (c) placing a suitable catholyte in the cathode compartment; and (d) allowing the neutral red-mediated conversion of chemical reducing power to electricity.

It is an object of the invention to provide methods that allow the interconversion of biochemical reducing power (e.g., NADH), biological energy (ATP), and electrical energy in an electrochemical bioreactor or fuel cell.

It is a further object of the invention to provide an economical method of promoting cell growth or production of desired products using electrically reduced neutral red.

Another object of the invention is to provide a method for converting biological reducing power into electricity.

It is an advantage of the present invention that electrical energy may be used to promote cell growth or fermentation or enzymatic transformation in the presence of neutral red.

Another advantage of the invention is that neutral red promotes the generation of electrical energy from waste material comprising mixed bacterial populations.

Other objects, features, and advantages of the present invention will be apparent on review of the specification and claims.

DETAILED DESCRIPTION OF THE INVENTION

Figure 1:
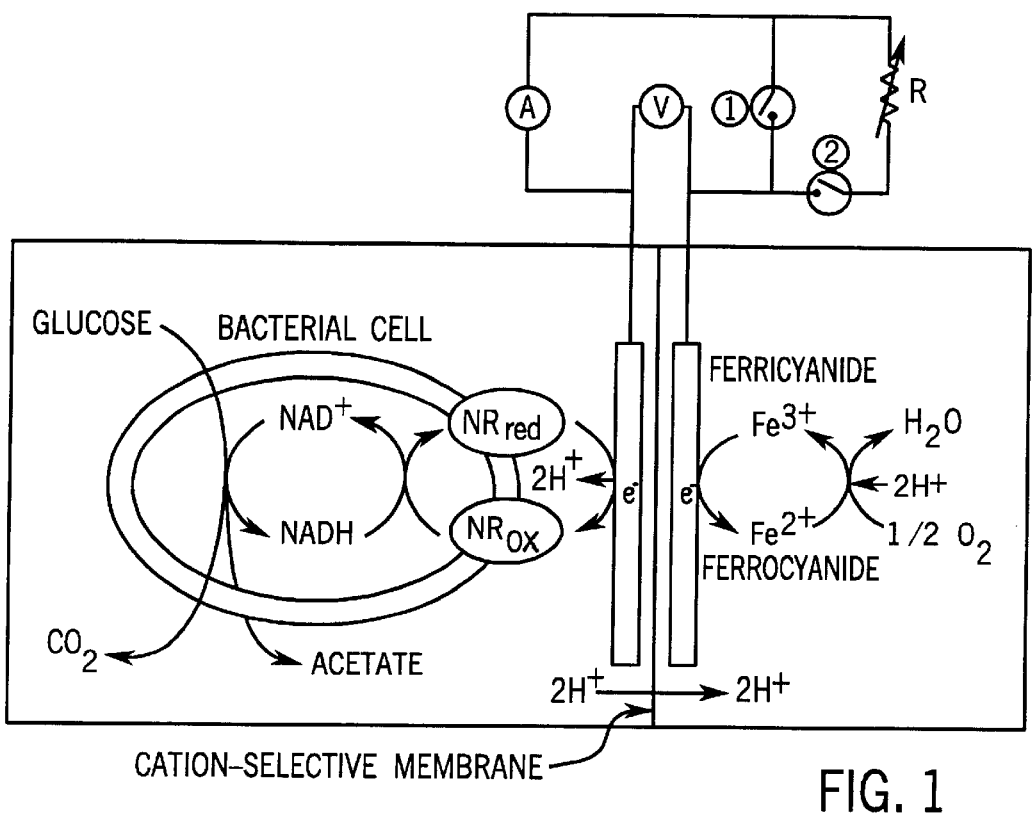
FIG. 1 is a schematic diagram of a microbial fuel cell using neutral red (NR) as an electronophore.

The present invention provides methods for achieving the efficient interconversion of chemical and electrical energy using neutral red. One aspect of the invention is a method for using electrical energy as a source of reducing power in fermentation or enzymatic reactions. Another aspect of the invention includes a method of using neutral red and cells or enzymes to produce electricity.

The invention is based on the discovery that the use of neutral red in methods directed toward regulating electron flow in biological systems offers a number of surprising advantages, which are disclosed in related U.S. Ser. Nos. 60/092,190 and 60/092,191; Park and Zeikus, *J. Bacteriol.* 181:2403–2410, 1999; and Park, et al. *Appl. Environ. Microbiol.* In press, all of which are incorporated by reference in their entirety.

A critical factor for the control of end-product yields in fermentation or enzymatic biotransformation reactions is regulation of electron distribution through the NADH/NAD$^+$ ratio. If additional reducing power (e.g., H$_2$ or electrochemically produced reducing equivalents) is supplied to bacteria, an increase in the NADH/NAD$^+$ ratio and metabolism may be expected. However, efficient transfer of electrons from electricity to NAD$^+$ requires a suitable electron mediator.

As discussed in detail in U.S. Ser. Nos. 60/092,190 and 60/092,191, neutral red was discovered to be a particularly good electron mediator for use in the interconversion of electricity and metabolic reducing power in electrochemical bioreactor systems. Neutral red is able to form a reversible redox couple at the electrode and has a highly negative $E_0'$. The $E_0'$ value for neutral red is very similar to that of physiological electron carriers in the electron transport chain, including, for example, NADH. The ability of neutral red to accept electrons from far up the electron transport chain enhances electricity production in biofuel cell systems. Neutral red is soluble at a neutral pH, it is stable in both its oxidized and reduced forms, it does not decompose during long-term redox cycling.

As disclosed in U.S. Ser. Nos. 60/092,190 and 60/092,191, neutral red is relatively nontoxic, and can be easily adsorbed on the cytoplasmic membrane of the cells under study, where it functions as an electronophore, or electron shuttle, for electron transfer across the cytoplasmic membrane. Neutral red was demonstrated to function as an electron mediator in reversible oxidation or reduction of compounds and to substitute for menaquinone in the cell membrane. Surprisingly, electrically reduced neutral red promotes growth, proton translocation and metabolite production in cells even in the absence of other sources of reducing power.

One aspect of the present invention provides a method for promoting reductive processes in a bioreactor system comprising the steps of (a) providing an electrochemical bioreactor system having a cathode compartment equipped with a cathode and an anode compartment equipped with an anode, the cathode and anode compartment being separated by a cation selective membrane, wherein the cathode and anode are connected by a conductive material to a power supply; and (b) placing a suitable amount of neutral red and a biological catalyst in the cathode compartment.

Preferably, the biological catalyst is selected from the group consisting of microbial cells, plant cells, animal cells, isolated intact cytoplasmic membranes, solubilized cytoplasmic membranes, and an enzyme having NADH or NADPH a cofactor. To maximize the efficiency of the interconversion of biochemical and electrical energy, the biological catalyst is immobilized on the cathode.

In a preferred embodiment, the method of the invention further comprises the steps of (c) placing an anolyte solution in the anode compartment; (d) delivering to the cathode an electric current of suitable strength to cause reduction of at least a portion of oxidized neutral red in the cathode compartment; and (e) allowing the reduced neutral red to transfer electrons to an oxidized substrate or an electron carrier.

The method of the invention is very versatile, in that it can be adapted for use with any number of biological catalysts, including microbial, plant, or animal cells, isolated intact cell membranes, solubilized cytoplasmic membranes, or a preparation of an enzyme that uses NADH or NADPH as a cofactor. Most conveniently, the biological catalyst comprises substantially pure or mixed cultures of cells, or an enzyme preparation. Preferably, the biological catalyst is capable of promoting the reduction of an oxidized substrate to a commercially or industrially important product, such as succinate, methane, or alcohols.

When whole cells are used as the biocatalyst, electrically reduced neutral red promotes cell growth or formation of a reduced product by chemical reduction of an $NAD^+$ or $NADP^+$ cofactor, or by serving as an electronophore. Preferably, the bioreactor system is one in which the electrically reduced neutral red promotes cell growth, ATP synthesis, or formation of a reduced product by chemical reduction of an $NAD^+$ or $NADP^+$ cofactor or by functioning as an electronophore.

In the examples below, electrically reduced neutral red is shown to promote the reduction of fumarate to form succinic acid in fermentation reactions using *Actinobacillus succinogenes* in a bioreactor system. Because succinic acid is an important fermentation product having many industrial uses, there is interest in developing a more. efficient fermentation process with enhanced succinic acid yields.

It was discovered that including electrically reduced neutral red during growth of *A. succinogenes* on glucose medium in a bioreactor system promotes fumarate reduction by chemically reducing $NAD^+$. Furthermore, neutral red promotes succinic acid production through its function as an electron mediator and electronophore. The electrical reduction of neutral red ($E_0'=-0.325$ volt) is chemically linked to $NAD^+$ reduction, and it is biochemically linked to generation of a proton motive force and succinate production. Neutral red appears to function by replacing menaquinone ($E_0'=-0.073$ volt) in the membrane bound fumarate reductase complex. Preferably, the reduced neutral red is able to increase cell growth by at least 10%, 20%, or even as much as 40% or more, relative to a comparable bioreactor system lacking neutral red. Electrically reduced neutral red is able to increase glucose or fumarate consumption by at least 25%, 50%, or 100% or more. Succinate production is increased by about 10% or even as much as 25% or more, relative to the production levels observed in a comparable bioreactor system lacking neutral red.

Similarly, electrically reduced neutral red is able to substitute for $H_2$ in promoting the growth of methanogenic bacteria and the reduction of $CO_2$ to methane by methanogenic archea. Preferably, the method of the invention increases growth of archea or methane production by at least about 25%, 50%, 100% or even as much as 300% or more.

It is reasonable to expect that the method of the present invention may be used with a wide range of biocatalysts to promote cell growth or the formation of reduced products in electrochemical bioreactor systems. It is envisioned that the method can be used with a variety of bacteria, archea, plant cells or animal cells.

It is expected that enzyme preparations may also be used in the practice of the invention. A desired enzyme may be partially purified using standard methods known to one of ordinary skill in the art. The enzyme may be isolated from its native source or from a transgenic expression host, or obtained through a commercial vendor.

Useful enzymes include any enzyme that can use reducing power from electrically reduced neutral red to form a desired reduced product, or which can transfer reducing power to neutral red and form a desired oxidized product. Most commonly, this reduction is mediated by NADPH or NADH. It is reasonably expected that any oxidoreductase may be used in the practice of the invention. For example, isolated alcohol dehydrogenases could be used in a bioreactor system comprising electrically reduced neutral red, $NADP^+$ or $NAD^+$, and a ketone, aldehyde or carboxylic acid that can serve as a substrate for the enzyme to form a more reduced end product such as an alcohol. Another example of a useful enzyme is carboxylic acid reductase, which uses NADPH and ATP to convert a carboxylic acid to reduced products (U.S. Ser. No. 5,795,759, herein incorporated by reference). One skilled in the art would appreciate that most enzyme-catalyzed reactions are reversible, and that there may be applications in which one would wish to use an oxidoreductase to obtain a desired oxidized substrate by the method of the present invention.

In the electrochemical bioreactor used in the present invention, the biocatalyst and neutral red are preferably immobilized on the cathode. In the case of whole cell biocatalysts, self-immobilization on a fine woven graphite felt electrode was found to take place. Immobilization of the biocatalyst may be achieved using any suitable method. Numerous techniques for immobilizing biocatalysts are known to the art (for example, see Woodward and Spokane, Analytical Enzymes: Biosensors in Industrial Enzymology, 2d Edition, p. 51–59, incorporated by reference herein). One wishing to immobilize a biocatalyst in the practice of the present invention could do so placing the biocatalyst, neutral red, and pyridine nucleotide cofactor between an electrode and an outer membrane (e.g., a polymer membrane) such that the biocatalyst, cofactor, and neutral red are sandwiched between the electrode and membrane. Alternatively, biocatalyst, neutral red, and pyridine nucleotide cofactor could be embedded in a matrix polymer and coated onto the electrode.

One of ordinary skill in the art wishing to practice the present invention could readily prepare an electrochemical bioreactor or fuel cell using the teachings disclosed herein. It should be appreciated that certain modifications to the disclosed bioreactors and fuel cells are well within the ability of one skilled in the art.

Catholytes and anolytes that may be used in electrochemical bioreactors or in fuel cells are provided in the examples. Catholytes that have been found to be suitable in electrochemical bioreactors include bacterial growth media or a phosphate buffer (50–100 mM, pH 7.0–7.2). Other suitable catholyte buffers for used in an electrochemical bioreactor include any catholyte that is non-denaturing to cells or enzymes.

A phosphate buffer comprising saline has been found to be suitable for use in an electrochemical bioreactor (100 mM sodium phosphate (pH 6.0) and 100 mM NaCl. A suitable anolyte may include any anolyte that is nondenaturing to cells or enzymes.

For a fuel cell, neutral red (100 $\mu$M) and a bacterial cell suspension in 50 mM phosphate buffer (pH 7.0) was found to be a suitable anolyte, with 100 mM phosphate buffer (pH 7.0) and 50 mM ferricyanide as the catholyte.

In both the electrochemical bioreactor systems and the fuel cell system described in the examples, the cathodic and anodic compartments were separated by a Nafion cationic selective membrane septum that allows the passage of protons and cations only. A suitable membrane for separating the cathodic and anodic compartments can be any membrane that allows transfer of only protons or cations across the membrane.

In the electrochemical bioreactor systems described in the examples below, the electrodes were made from fine woven graphite felt. The woven graphite felt offers the advantage of providing a large surface area electrode that permits immobilization of the biocatalyst over a large area. However, other materials may be suitable for electrodes, including conductive polymers and metallic materials.

The electrodes were connected to a power source or to a multimeter using a platinum wire. Other materials suitable for connecting the electrodes to the power source or multimeter include conducting polymers or metallic materials.

In the electrical bioreactors described below, the current between the anode and cathode was between about 0.4 and about 2.0 mA, with the voltage being about 1.5 V. It is envisioned the present invention could be practiced using currents of from about 0.004 to about 200 mA.

In the fuel cell system, the resistance from the anode and cathode was about 1,000 ohms. It is envisioned that resistances of from about 10 to about 10,000 ohms could be used in the practice of the invention.

Neutral red was included in the catholyte of electrochemical bioreactors and in the anolyte of fuel cell systems at a concentration of about 100 $\mu$M. It is expected that neutral red concentrations of between about 1 and 1000 $\mu$M would be suitable in the practice of the invention.

Neutral red can also be used as an electron mediator in the conversion of energy derived from the metabolism of growing or resting bacterial cells to electricity.

Using *Actinobacillus succinogenes* 130Z growing cells in a fuel cell system that had neutral red as the electron mediator and ferricyanide as the electron acceptor, the maximum current produced using was 2.17 mA, and the potential was <100 mV in a closed circuit configuration. After 20 hour cultivation, the fuel cell system was converted from a closed to an open circuit system. The potential rapidly reached the theoretical maximum value of 0.685 volt (i.e. the redox potential difference between NR).

A comparison of the efficacy of NR and thionin as electron mediators made using *A. succinogenes* resting cells as the catalyst revealed that much more electricity was produced with NR than with thionin as the electron mediator.

When NADH, NR, and ferricyanide were used as the electron donor, electron mediator, and electron acceptor, respectively, the current produced was proportional to NADH concentration. In a system that employed *E. coli* K-12 as the catalyst, the currents and voltages produced were similar to those obtained using *A. succinogenes* as the catalyst. The current and voltage were found to increase with increasing glucose concentrations.

Anaerobic sewage sludge was also used as the catalyst in a fuel cell system. The voltage and current produced in fuel cells using sewage sludge as the catalyst were comparable to those produced using *E. coli* and Actinobacillus, and they were stable for 120 hours in a closed circuit system with a 2.2 K ohms external resistance.

It is expected that growing or resting cells of types other than those described in the examples can be used as catalysts in a fuel cell system to generate electricity by the method of the present invention. Depending on the particular cell chosen as a biocatalyst, reducing power used in the generation of electricity may include light, inorganic compounds, or organic compounds, or any other energy source that cells are able to use for growth or metabolism.

It is envisioned that the neutral red-mediated interconversion of biochemical and electrical energy may be adapted for use in a number of different applications. For example, neutral red oxidoreduction can be used to detect electrical levels in biosensor systems using whole cells or enzymes.

Accordingly, the invention includes a method for detecting the presence of a specific organic or inorganic test compound in a sample comprising the steps of (a) providing biosensor comprising an electrochemical fuel cell system having an anode compartment and a cathode compartment separated by a cation-selective membrane, wherein each compartment is equipped with an electrode, wherein the electrodes are connected by a wire to a multimeter; (b) placing an anolyte in the anode compartment, the anolyte comprising the sample, a suitable concentration of neutral red, and a biological catalyst comprising microbial cells and an enzyme, wherein the biological catalyst is able to oxidize the test compound; (c) placing a suitable catholyte in the cathode compartment; and (d) allowing oxidation of at least a portion of any test compound present in the sample and reduction of at least a portion of oxidized neutral red; (e) allowing the transfer of electrons from reduced neutral red to the cathode; (f) detecting the generation of an electrical current.

In cell or enzyme biosensors known to the art, the presence of a chemical (e.g., glucose) is detected using an enzyme (glucose oxidase) in a membrane-based electrode system. In the example of glucose and glucose oxidase, the enzyme-catalyzed reaction consumes $O_2$ and produces peroxide. Therefore, glucose present in the sample is correlated with a decrease in $O_2$ concentration and an increase in peroxide concentration, either one of which be detected by a specific electrode. By the method of the present invention, electrical current generated can be measured directly. In the neutral red system, a specific compound in an unknown test sample is tested using cells or enzymes that are capable of oxidizing the compound to generate a detectable current upon oxidation of the compound by the biocatalyst. Therefore, the concentration of the compound can be determined by measuring the electricity generated upon oxidation of the test compound. It is well within the ability of one skilled in the art wishing to detect a particular compound to adapt the method of the present invention to detect the compound by selecting a suitable biocatalyst capable of oxidizing the compound.

Another important application using neutral red provides a method for measuring the chemical oxygen demand in waste water comprising (a) providing an electrochemical fuel cell system comprising an anode compartment and a cathode compartment separated by a cation-selective membrane, wherein each compartment is equipped with an electrode, wherein the electrodes are connected by a wire to a multimeter; (b) placing an anolyte in the anode compartment, the anolyte comprising a suitable concentration of neutral red and waste water comprising or supplemented with a biological catalyst; (c) placing a suitable catholyte in the cathode compartment; (d) allowing the neutral red-mediated conversion of chemical reducing power to electricity; (e) measuring the electrical current generated by the fuel cell system.

The following nonlimiting examples are intended to be purely illustrative.

EXAMPLES

Example 1

Electrically Reduced Neutral Red Promotes the Reduction of Fumarate to Succinic Acid Chemicals and Reproducibility of Results All chemicals were reagent grade and gases were purchased from AGA Chemicals (Cleveland, Ohio, USA). All individual experiments were repeated two to three times with identical results.

Electrochemical Bioreactor Systems

The ECB system I (40 ml working volume) was used for enzymatic and chemical reduction tests and ECB system II (300 ml working volume) was used for electrical-dependent cultivation of cells. The ECB systems, specially designed for maintaining anaerobic conditions and for growing bacteria, were made from Pyrex glass by the MSU Chemistry Department, East Lansing, Mich., USA. The ECB system was separated into anode and cathode compartments by a cation selective membrane septum (diameter [$\phi$]=22 mm for type I and [$\phi$]=64 mm for type II) (Nafion, Electrosynthesis, Lamcosta, N.Y.); 3.5 $\Omega cm^{-2}$ in 0.25 N NaOH). Chemicals and metabolites cannot be transferred across the Nafion membrane; only protons or cations transfer. Both the anode and cathode were made from graphite fine woven felt (6 mm thickness, 0.47 $m^2 g^{-1}$ available surface area (Electrosynthesis, NY, USA). A platinum wire ([$\phi$]$\Omega$ 0.5 mm, <1.0 $\Omega cm^{-2}$; Sigma, St. Louis, Mo., USA) was attached to the graphite felt using graphite epoxy (<1.0 $\Omega cm^{-2}$, Electrosynthesis, NY, USA). The electric resistance between anode and cathode was <1 k$\Omega$. The weight of both electrodes was adjusted to 0.4 g (surface area, 0.188 $m^2$) for system I and 3.0 g (surface area, 1.41 $m^2$) for system II. The current and voltage between anode and cathode were measured by precision multimeter (Fluke model 45, Everett, Wash., USA) and adjusted to 0.3–2.0 mA and 1.5 volt for system I, and 1.0–10.0 mA and 2.0 volt for system II, respectively. The electrochemical half oxidation of $H_2O$ was coupled to half reduction of NR (100 $\mu M$) and the oxidation of reduced NR was coupled to bacteriological reduction of fumarate. $H_2$ was not produced under the electrochemical conditions used to reduce NR or MV. For tests in ECB system I, the cathode compartment contained the cell suspension, membrane suspension or solubilized membranes and the anode compartment contained 50 mM phosphate buffer (pH 7.2) and 100 mM NaCl. For growth studies in ECB system II, the cathode compartment contained the growth medium inoculated with A. succinogenes and the anode compartment contained 100 mM phosphate buffer (pH 7.0) and 100 mM NaCl.

Organism and Growth Conditions

A. succinogenes type strain 130Z is maintained at MBI International (Lansing, Mich., USA) (10, 39). Bacteria were grown in butyl-rubber-stoppered, 158 ml serum vials containing 50 ml medium with $CO_2$—N2 (20%–80%, 20 psi) gas phase, unless stated otherwise. The growth medium A contained the following (per liter of double distilled water): yeast extract, 5.0 g; $NaHCO_3$, 10.0 g; $NaH_2PO_4.H_2O$, 8.5 g; and $Na_2HPO_4$, 12.5 g. The pH of medium was adjusted to be 7.0 after autoclaving. Separately autoclaved solutions of glucose (final concentration 60 mM), and fumarate (final concentration 50 mM) were aseptically added to the medium after autoclaving. Media were inoculated with 5.0% (v/v) samples of cultures grown in the same medium and incubated at 37° C.

Preparation of Cell Suspensions

Bacterial cultivation, harvest and washing were done under strict anaerobic $N_2$ atmosphere as described previously (39). A 16 hour A. succinogenes culture was harvested by centrifugation (5,000×g, 30 minutes) at 4° C. and washed three times using a 1500 ml solution of 50 mM Na phosphate buffer (pH 7.2) containing 1 mM dithiothreitol (DTT). The washed bacterial cells were re-suspended in 50 mM sodium phosphate buffer with 2 mM DTT. This suspension was used as a catalyst for $H_2$-dependent and electrical-dependent reduction of fumarate to succinate; and, it was used for cyclic voltammetry and for NR absorption to cells.

Electrochemical Reduction of $NAD^+$ or $NADP^+$

ECB system I with 1 mM $NAD^+$ or $NADP^+$ and 100 ($\Omega$M NR or MV was used for electrochemical reduction of $NAD^+$ or $NADP^+$. The electrode potential and current were adjusted to 2.0 volts and, 1.0–3.0 mA, respectively. Ag/AgCl and platinum electrodes were used to measure the reactants redox potential to check if the reaction was progressing. Generally, the redox potential of a biochemical or electrochemical reaction is measured using an Ag/AgCl electrode ($E_0'$ of $[Ag/Ag^-]$, $\neq$+0.196 volt) or a Calomel electrode ($E_0'$ of $[Hg/Hg^+]$, +0.244) as a reference electrode but it has to be expressed as the potential vs. natural hydrogen electrode (NHE), which is used for thermodynamical calculation of organic or inorganic compounds (e.g., $E^{0'}$ of $NADH/NAD^+$ is a −0.32 volt and $H_2/2H^+$ is −0.42 volt). A potential measured using Ag/AgCl electrode is converted to potential vs. NHE by adding +0.196 volt to the measured potential ($E_0'$ vs. NHE=$E_0'$ vs. Ag/AgCl+0.196). Oxygen was purged from the reactants and from the redox dye solution in 50 mM Tris-HCl (pH 7.5) by bubbling with oxygen free nitrogen for 10 minutes before supplying electricity. The NADH concentration in the reactant was spectrophotometrically measured at 340 mm and calculated using the millimolar extinction coefficient 6.23 $mM^{-1} cm^{-1}$. NADH or NADPH production was confirmed by absorption spectra data at each sampling time.

Preparation of Purified Membranes, Solubilized Membranes and Membrane Free Cell Extract Cell free extracts were prepared at 4° C. under an anaerobic $N_2$ atmosphere, as described previously (Van der Werf, et al., 1997, Arch. Microbiol. 167:332–342). The harvested and washed cells were resuspended in 50 mM phosphate buffer (pH 7.2) containing 1 mM DTT and 0.05 mg/ml deoxyribonuclease. Cells were disrupted by passing twice through a French Press at 20,000 psi. The cell debris was removed by centrifugation three times at 40,000×g for 30 minutes. The purified membranes were obtained from the cell free extracts by centrifugation at 100,000×g for 90 minutes. The supernatant was decanted and saved as the membrane-free cell extract. The brown and clear precipitate was washed twice with 50 mM phosphate buffer (pH 7.2) and re-suspended in the same buffer by homogenization. Solubilized membranes were obtained from membrane fraction by Triton X-100 extraction (Lemire, et al., 1983, *J. Bacteriol.* 155:391–397). Triton X-100 was added to a final 1% (v/v) concentration and, the suspension was incubated for 3 hours. Triton-solubilized protein was recovered after removing insoluble debris by centrifugation at 100,000×g and 4° C. for 90 minutes.

Neutral Red Binding to Cells and Membranes

The absorption of redox dyes to cells and purified membranes was determined by measuring the residual NR and MV in solution after mixing with cells or membrane suspensions for 30 minutes at 37° C. Bacterial cell suspensions ($OD_{660}$ between 0–3.0) and the purified membrane suspension (0–10 mg/ml protein) were used to analyze redox dye absorption (i.e., binding). NR solutions (50 $\mu$M and 25 $\mu$M) and MV (100 $\mu$M) were used for measuring dye binding to intact cells and membranes. MV (100 $\mu$M) was used for cell binding. The cells and membranes were removed from the reaction mixture by centrifugation at 12,000×g for 10 minutes and by ultracentrifugation at 150,000×g for 20 minutes, respectively. The NR concentration was calculated using a calibration curve spectrophotometrically pre-determined at 400 nm and pH 7.2, and MV was determined using the millimolar extinction coefficient (578) 9.78 $mM^{-1}$ $cm^{-1}$ after reduction by addition of Elepsiden 1.5 mM dithionite at pH 7.2 (Lissolo, et al., 1984, *J. Biol. Chem.* 259:11725–11729). The protein concentration of membrane suspensions was determined by a calibration curve (protein concentration, mg/ml=$A_{595}$×1.3327) using Bradford Reagent (Bio-Rad, Hercules, Calif., USA).

Measurement of Proton Translocation

Proton translocation was measured under an anoxic $N_2$ atmosphere. $H_2$-dependent proton translocation by cell suspensions was measured as described by Fitz and Cypionka (Fitz, et al., 1989, *Arch. Microbiol.* 152:369–376). Electrical-dependent proton translocation was measured in an electrochemical bioreactor system designed for measurement of proton translocation. The tube ([ɸ] 10 mm ID and 90 mm length) with a Vycor tip (ion exchangeable hard membrane, Bas, West Lafayette, Ind., USA) was used as an anode compartment and a graphite rod ([ɸ] 7 mm×70 mm) was used as an anode, and 0.05 g graphite felt (surface area, 0.0235 $m^2$) was used as a cathode. The pH electrode (Orion 8103 ROSS) was placed in the cathode compartment and was connected to a recorder (Linear) via a pH meter (Corning, 130) that converted the proton pulse into a recordable signal. Cell suspensions were made in KKG solution (pH 7.1) which contains 100 mM KSCN, 150 mM KCl and 1.5 mM glycylglycin and placed in the cathode. The anode contained a 50 mM phosphate buffer with 50 mM KCl as an anolyte. The total volume and working volume of the cathode and anode compartments were 30 ml and 5.5 ml, respectively, The working potential and current between anode and cathode were 2.0 volt and 0.3–0.35 mA for experiments using electrical reducing power and NR. Bacterial cells were cultivated for 16 hours in medium A with fumarate-$H_2$ or glucose. The cells were anaerobically harvested by centrifugation at 5,000×g and 20° C. for 30 minutes and washed twice with 100 mM KCl. The cells were modified with 100 $\mu$M NR to measure electrical-dependent proton translocation and washed again with 100 mM KCl. The washed bacteria ($OD_{660}$, 10) were re-suspended in $N_2$-saturated 150 mM KCl. Cell suspensions were allowed to equilibrate for 30 minutes at room temperature. The incubated cells were centrifuged at 5,000×g and 20° C. for 30 minutes and re-suspended in KKG solution and then the incubation was continued for 30 minutes under $H_2$ atmosphere before the measurement of proton translocation. To measure electrical-dependent proton translocation upon fumarate addition, the cell suspension was incubated in the presence or absence of HOQNO in the cathode compartment under $N_2$ atmosphere and charged with 2.0 volt electrode potential for 20 minutes.

Enzyme Assays

Enzyme activity measurements were performed under an anaerobic $N_2$ atmosphere, as described previously (Van der Werf, et al., 1997, *Arch. Microbiol.* 167:332–342). The membrane-free extract, purified membrane and solubilized membrane preparations described above were used to assay hydrogenase, diaphorase, and fumarate reductase activities. Fumarate reductase (EC 1.3.) and hydrogenase (EC 2.12.2.2.) activities were measured as described by van der Werf (1997, *Arch. Microbiol.* 167:332–342), with a Beckman spectrophotometer (Model, DU-650). Diaphorase activity with $BV2^+$ and $NR^+$ was measured under analogous conditions with hydrogenase using NADH (0.6 mM) instead of $H_2$ as electron donor (Schneider, et al., 1984, *Eur. J. Biochem.* 142:75–84). The oxidation and reduction of benzyl viologen and NR were spectrophotometrically measured at 578 nm and 540 nm, and the oxidation and reduction of NAD(H) were spectrophotometrically measured at 340 nm. Reduced benzyl viologen was prepared as described previously (Lissolo, et al., 1984, *J. Biol. Chem.* 259:11725–11729). The millimolar extinction coefficient of benzyl viologen (578), NR (540) and NAD(H) (340) were 8.65 $mM^{-1}$ $cm^{-1}$, 7.12 $mM^{-1}$ $cm^{-1}$, and 6.23 $mM^{-1}$ $cm^{-1}$, respectively.

Enzymatic Analysis of Fumarate Reduction Membranes and Solubilized Membrane

Membrane suspensions (3.25 mg/ml protein) and solubilized membranes (3.2 mg/ml protein) were used as the enzyme sources. Serum vials (50 ml) and ECB system I was used for $H_2$-dependent and electrical dependent reduction of fumarate to succinate, respectively. Anaerobically prepared 50 mM fumarate in 50 mM phosphate buffer (pH 7.2) was used as reactant and catholyte, and 100 mM phosphate buffer with 100 mM NaCl (pH 7.0) was used as anolyte. The reaction was started by the addition of enzyme sources and it was maintained at 37° C. Substrate and product concentrations were analyzed by HPLC (Guerrant, et al., 1982, *J. Clin. Microbiol.* 16:355–360). The influence of HOQNO on fumarate reduction in cell suspensions and membranes were analyzed as follows.

Cell suspensions ($OD_{660}$=4.2) and membrane suspension (2.65 mg/ml protein) were used as the enzyme sources. Serum vials (50 ml) and ECB system I was used for $H_2$-dependent and electrical dependent reduction of fumarate to succinate, respectively. Anaerobically prepared 50 mM fumarate in 50 mM phosphate buffer (pH 7.2) was used as reactant and catholyte and 100 mM phosphate buffer with 100 mM NaCl (pH 7.0) was used as analyte. 2 $\mu$M HOQNO was used as an inhibitor for menaquinone. The reaction was started by the addition of enzyme sources and it was maintained at 37° C. Substrate and product concentration was analyzed by HPLC.

Cyclic Voltammetry

A 3 mm diameter glassy carbon working electrode (BAS, West Lafayette, Ind., USA), platinum wire counter electrode (BAS), and an Ag/AgCl reference electrode (BAS) were used in an electrochemical cell with a working volume of 2 ml. Cyclic voltammetry was performed using a cyclic voltametric potentiostat (BAS, model CV50W) linked to an IBM microcomputer data acquisition system. Prior to use, the working electrode was polished with an alumina/water slurry on cotton wool, and the electrochemical cell was thoroughly washed. Oxygen was purged from the cell suspension, membrane suspension, or solubilized membrane solution by bubbling with oxygen free $N_2$ for 10 minutes before electrochemical measurements. Bacterial suspensions ($OD_{660}$=3.0), membrane suspensions (2.54 mg protein/ml), and solubilized membranes (3.2 mg protein/ml) were used as enzyme sources. The scan rate used was 25 mV/s over the range −0.3 to −0.8 volt 50 mM phosphate buffer containing 5 mM NaCl was used as electrolyte. NR $\mu$100 (M) and 50 mM fumarate was used as the electron mediator and the electron acceptor, respectively.

Growth Analysis

Growth of cells suspended in the medium was determined by measuring the suspensions (optical density at 660 nm), the growth yield of cells absorbed onto the electrode was determined by measuring protein concentration. The protein concentration was converted to optical density using a predetermined calibration curve (bacterial density=protein concentration, mg/ml×1.7556). The cathode, on which the bacteria absorbed, was washed three times, by slow agitation, in 300 ml of phosphate buffer (50 mM, pH 7.0) for 30 minutes. The bacterial lysate was obtained from electrodes by alkaline treatment at 100° C. for 10 minutes using 1N—NaOH. After removing cell debris from the lysate by centrifugation at 10,000×g and 4° C. for 30 minutes, the protein concentration of the bacterial lysate was determined using Bradford Reagent (Bio-Rad, Hercules, Calif., USA), and a predetermined calibration curve (protein concentration, mg/ml=$A_{595}$×1.3327).

Methanogenic Granules Growth and Metabolic Analysis

Methanogenic granules containing mixed cultures of fatty acid-degrading syntrophiles and methanogens were obtained from a bench scale anaerobic sludge reactor fed on a mixture of 50 mM acetate, butyrate, and propionate in MBI International (Lansing, Mich.) (Wu, et al., 1993, *Arch. Microbiol.* 39:795–803 and Wu, et al., 1993, *Appl. Mirobiol. Biotechnol.* 39:804–811). Methanogenic granules were cultivated in PBBM prepared without organic compounds (Kenealy, et al., 1981, *J. Bacteriol.* 146:133–140). The medium was prepared without phosphate, brought to pH 7.2 with NaOH, boiled, sparged with $N_2$—$CO_2$ (80:20%) or $H_2$—$CO_2$ (80:20%), dispensed into 158-ml Wheaton serum vials, sealed with butyl rubber stoppers, and autoclaved. Phosphate, sulfide (0.01%), $N_2$—$CO_2$ (80:20%) or $H_2$—$CO_2$ (80:20%), and vitamin solution were added after autoclaving. The medium volume was 40 ml, and the initial head space gas pressure in serum vials was adjusted to 30 psi. Media were inoculated with 3.0% (by volume; protein concentration, 1.995 mg/ml) methanogenic granules and incubated at 37° C. All procedures for medium preparation, inoculation, and cultivation were the same as those used for vial cultures except that $Na_2S$ was not added because the medium was electrically reduced. $Na_2S$ (2%) was added to the anode compartment as reducing agent to remove the $O_2$ generated. NR (100 M) was added to the cathode compartment as electron mediator. The current and potential between anode and cathode were 0.4 mA and 2.0 volts. $CO_2$ and $CH_4$ were analyzed using a gas chromatograph equipped with a carbosphere column and flame ionized detector. The injector and column temperatures were 50° C. and 150° C., respectively, and the carrier ($N_2$) flow rate was 45 ml/min. Gas samples were removed with a pressure lock syringe. $CO_2$ consumption and $CH_4$ production are shown as the percentage of total gas composition in the headspace.

Bacterial Growth and Cell Preparation for Generating Electricity

*A. succinogenes* 130Z and *E. coli* K-12 were anaerobically grown for 16 hours and 20 hours, respectively, in medium A (10 g/L glucose, 5 g/L yeast extract, 8.5 g/L $NaH_2PO_4$, and 10 g/L $NaHCO_3$) under an anaerobic $N_2$—$CO_2$ (80:20) atmosphere at 37° C. in 150 ml serum vials or under a $N_2$ (100%) atmosphere in fuel cell system with a pH controller. The inoculum size was 3% (v/v) for both vial and fuel cell experiments. Resting cell suspensions were prepared by harvesting stationary phase cultures at 4° C. by centrifugation at 5,000×g. The cells were washed twice using 50 mM phosphate buffer (pH 7.0) under a 100% $N_2$ atmosphere. The washed cells were resuspended in 50 mM phosphate buffer (pH 7.0), then dissolved $O_2$ was removed by gassing with $N_2$ for 30 minutes. The cell density was adjusted to $OD_{660}$ 3.0.

Fuel Cell Systems for Growing or Resting Cells

A two-compartment (anode and cathode) electrochemical cell was used as a fuel cell system for microbial electricity production (FIG. 1). When switches one and two are off, there is an open circuit. When switch one is on and switch two is off, a closed circuit is formed. When switch one is off and switch two is on, a closed circuit with external variable resistance is formed. One hundred $\mu$M NR or 300 $\mu$M thionin were used as the electron mediator. The total and working volumes of each compartment were 1,600 ml and 1,300 ml, respectively. The electrodes, each made of 12 g fine woven graphite felt (0.47 $m^2$/g, Electrosynthesis, NY) were connected to a precision multimeter (Fluke model 45, Everett, Wash.) with a platinum wire ([ϕ]=0.5 mm, <1.0 $\Omega cm^{-2}$; Sigma, St. Louis, Mo., USA) using graphite epoxy (<1.0 $\Omega cm^{-2}$, Electrosynthesis, NY). Anode and cathode compartments were separated by a cation-selective membrane septum ([ϕ] 70 mm, Nafion, Electrosynthesis, NY). The self-electric resistance of the fuel cell system between the anode and cathode was approximately 1,000$\Omega$. The resistance was adjusted using variable resistance for controlling current production, but it was not adjusted for measuring maximum potential or current production. The current and voltage between the anode and cathode were measured by a precision multimeter (Fluke model 45, Everett, Wash.). The electrochemical half-reduction of ferric ion (as potassium ferricyanide, $E_0$(=+0.36 volt)—which was re-oxidized by $O_2$ ($E_0'$=+0.82 volt) was coupled to neutral red or thionin half-oxidation which was, in turn, reductively coupled to bacterial oxidative metabolism. In the fuel cell system using resting cells, the bacterial cell suspension ($OD_{660}$, 3.0) in 50 mM phosphate buffer (pH 7.2) containing 100 $\mu$M NR or 300 $\mu$M thionin, and 100 mM phosphate buffer (pH 7.0) containing 50 mM ferricyanide were used as the anolyte and catholyte, respectively. In the fuel cell system using growing cells, medium A containing a fresh bacterial inoculum was the anolyte; the catholyte was the same as for resting cells. During experiments, complete anoxygenic conditions were maintained in the anode compartment by gassing with 100% $N_2$ for 30 minutes before operation at $N_2$ flow rates of 0.8 ml/min. The trace oxygen contained in the $N_2$ gas was removed in a furnace filled with pure copper fillings at 37° C. The cathode compartment was oxygenated by constant air bubbling and stirring. The anode compartment was maintained at pH 7.0 using an automatic pH controller (New Brunswick Scientific Co., model pH-40, Edison, N.J.).

Current Production by Chemical Dye Chemical Oxidation Coupled to NADH Oxidation

A small chemical fuel cell system (total volume 50 ml; working volume 30 ml) consisting of an anode and cathode compartments equipped with 0.3 g fine woven graphite felt electrodes and a cation-selective membrane septum (Ω 20 mm, Nafion, Electrosynthesis) was used. A 100 μM NR solution in Nafion, Electrosynthesis) was used. A 100 μM NR solution in 50 mM phosphate buffer (pH 7.0) and 100 mM phosphate buffer (pH 7.0) containing 50 mM ferricyanide were used as the anolyte and catholyte, respectively. Oxygen was completely removed from the anode compartment by $N_2$ gassing for 30 minutes before adding NADH. The concentrated NADH solution in 50 mM phosphate buffer (pH 7.0) was previously gassed with $N_2$ to remove $O_2$.

Cyclic Voltametry

A 3 mm-diameter glassy carbon working electrode, a platinum wire counter electrode, and an Ag/AgCl reference electrode (all from BAS, West Lafayette, Ind.) were used in an electrochemical cell with a 3 ml working volume. Cyclic voltametry was performed using a cyclic voltametric potentiostat (model CV50W, BAS) linked to an IBM personal computer data acquisition system. Prior to use, the working electrode was polished with an aluminum/water slurry on cotton wool, and the electrochemical cell was thoroughly washed. Oxygen was purged from the reactant by bubbling with oxygen-free $N_2$ for 10 minutes before electrochemical measurement. The scanning rate used was 25 mV/s over the range −0.3 to −0.8 volt. A 50 mM phosphate buffer containing 5 mM NaCl was used as the electrolyte. One hundred μM NR and 100 μM NAD were used as the electron mediator and acceptor, respectively.

Generation of Electricity Using Anaerobic Sludge

The anaerobic sludge was obtained from the East Lansing sewage treatment plant (MI, USA). The fresh anaerobic sludge was settled under a $N_2$ atmosphere for one day to remove solid particles. The supernatant (1,200 ml) was used as biocatalyst and anolyte for the fuel cell system, to which 3 g/L glucose was added as energy source. The catholyte was 100 mM phosphate buffer (pH 7.0) containing 50 mM ferricyanide.

Results

Electricity Generation by Fuel Cells

The $E_o'$ values of the electron mediators used for converting the reducing power generated by microbial metabolic oxidation to electricity are important determinants of the maximum electricity amount that can be generated in microbial fuel cells. Chemical properties of artificial electron mediators (i.e., NR and thionin) with those of natural electron mediators (i.e., $NAD^+$ and menaquinone) are shown in Table 1. The electron driving force generated from using NR is far greater than from thionin when the redox dye is coupled to an oxidant (i.e., ferricyanide) in a chemical or microbiological fuel cell. This difference is due to differences between the $E_0'$ values for NR and thionin. Consequently, the $\Delta E_0$ generated from NR or thionin oxidation coupled to ferricyanide reduction is 0.645 volt (NR) and 0.296 volt (thionin). These a $\Delta E_0$ values are the theoretical maximum potentials produced in fuel cells using these electron mediators.

Figure 2A:
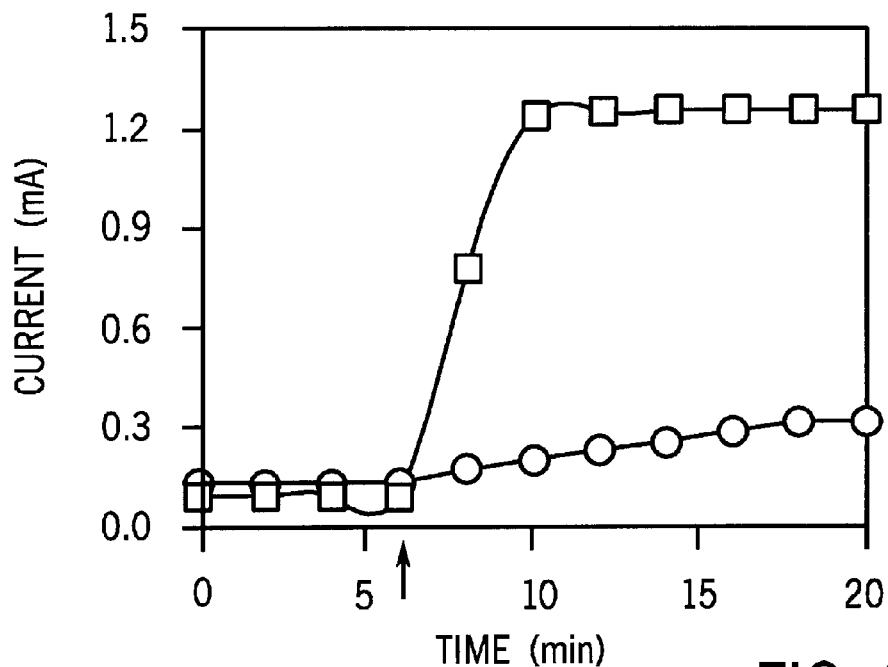
FIG. 2 shows the current production from NADH oxidation in a chemical fuel cell with NR (A) or thionin (B) as the electron mediator.
Figure 2B:
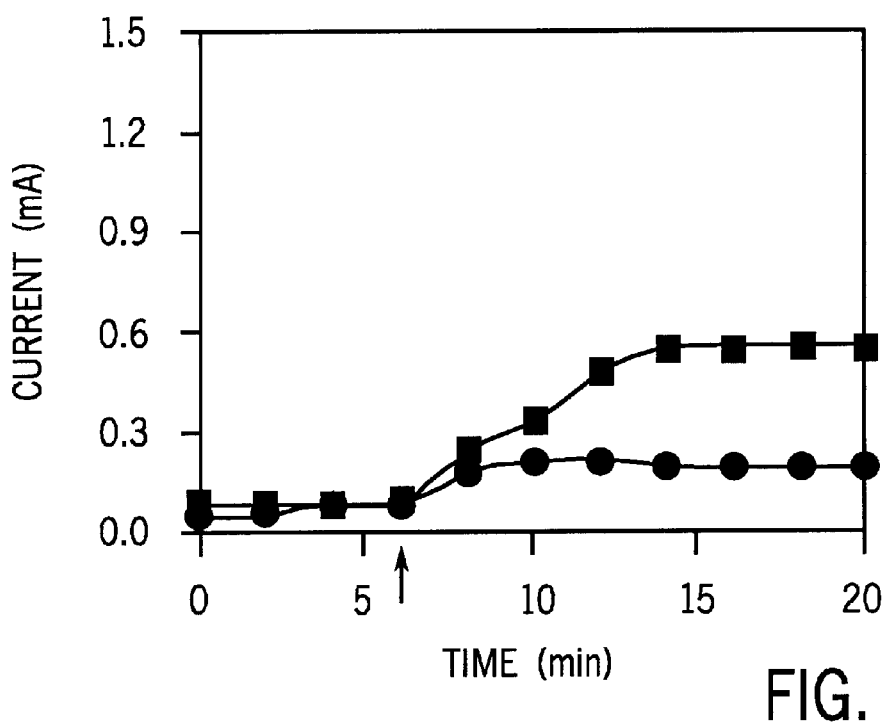

Results of experiments performed demonstrate the superiority of NR over thionin as an electron mediator and that reduced NR is able to donate electrons to the electrode for electricity production in a microbial fuel cell. FIG. 2 shows that the use of NR as an electron mediator in a chemical fuel cell generates higher current than that obtained using thionin, and that the current produced depends on the NADH concentration used. Arrows indicate the addition of 1 (circles) or 3.5 (squares) mM NADH. At low NADH concentrations the current was quite low. Although thionin reduction was faster than NR reduction when using NADH as the reductant, the mediator oxidation rate at the electrode is rate-limiting, because more current was produced with NR as the electron mediator.

TABLE 1

Redox mediators, their structural formula, redox potentials ($E_o'$), and maximum absorbance wavelength ($\lambda_{max}$).

| Structural formula | Redox mediator | $E_o'$ (V) | $\lambda_{max}$ |
|---|---|---|---|
| [phenazine structure with H₃C, H₃C, N, NH, N⁺–CH₃, CH₃] | Neutral Red | −0.325 | 540 |
| [phenothiazine structure with H₂N, S, N, N⁺H, H] | Thionine | +0.064 | 598 |
| [naphthoquinone structure with CH₃, R =, repeating isoprenoid unit] | Menaquinone | −0.074 | 260/280 |

TABLE 1-continued

Redox mediators, their structural formula, redox potentials ($E_o'$), and maximum absorbance wavelength ($\lambda_{max}$).

| Structural formula | Redox mediator | $E_o'$ (V) | $\lambda_{max}$ |
|---|---|---|---|
| 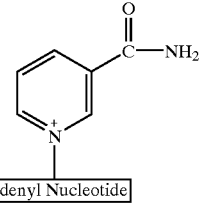 | NAD$^+$ | −0.32 | 340 |

Figure 3A:
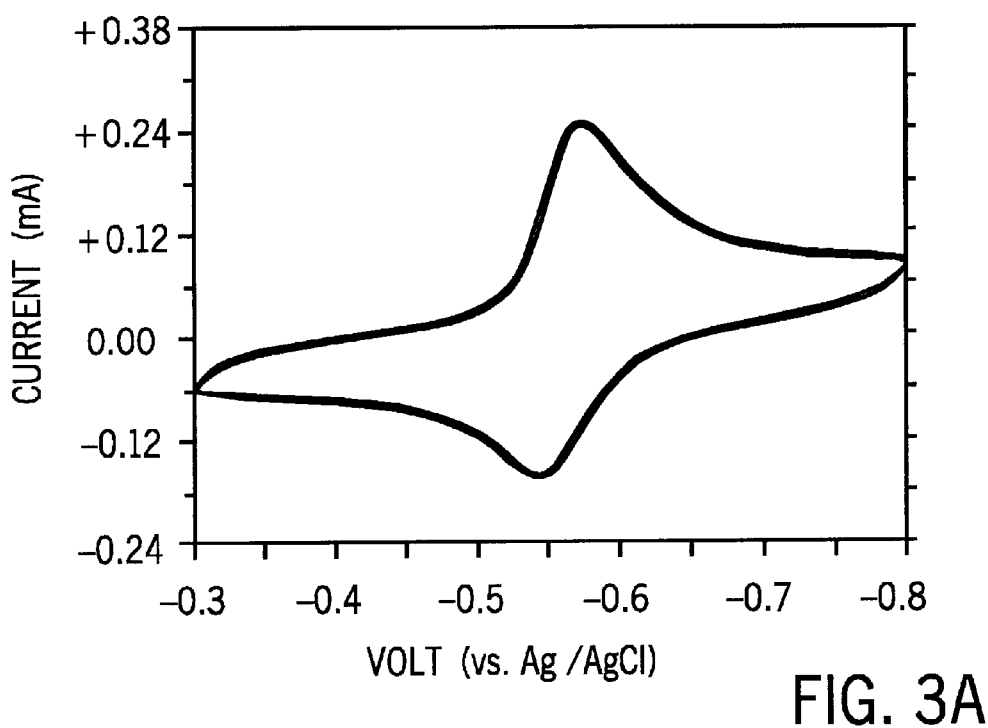
FIG. 3 is a cyclic voltammogram obtained with a glassy carbon electrode on successive cycles following introduction of the electrode into a 100 µM NAD$_+$ solution.
Figure 3B:
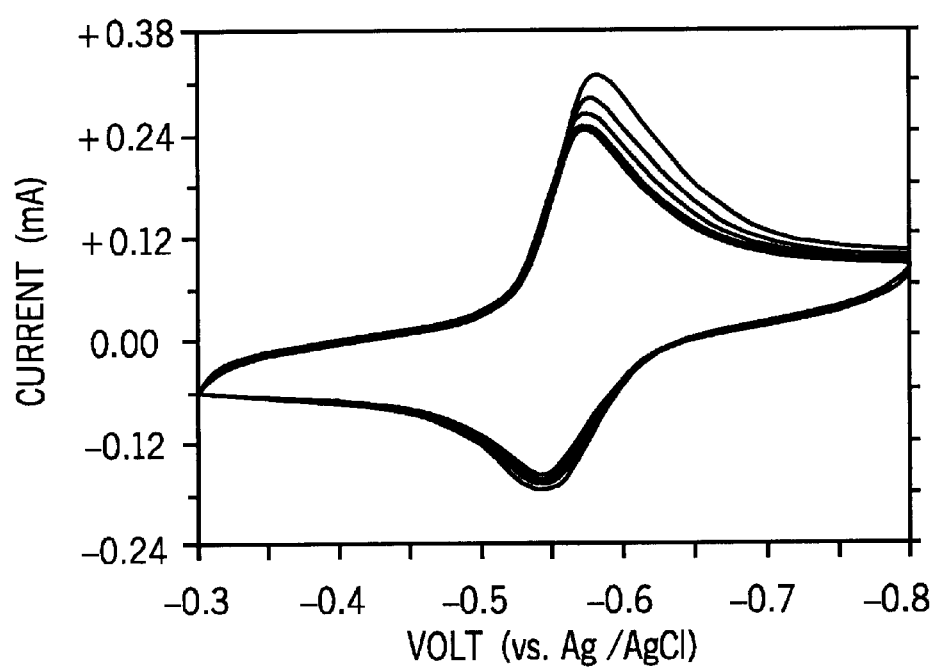

Cyclic voltammograms of a NR solution in the presence or absence of NAD$^+$ show that NR oxidation (upper) and reduction (lower) peaks did not shift during twenty scanning cycles in the absence of NAD$^+$ (FIG. 3A). Both peaks increased upon NAD$^+$ addition (FIG. 3B). NAD$^+$ enables more electrons to pass unidirectionally from the electrode to NR to NAD and from NADH to the electrode via NR.

Figure 4A:
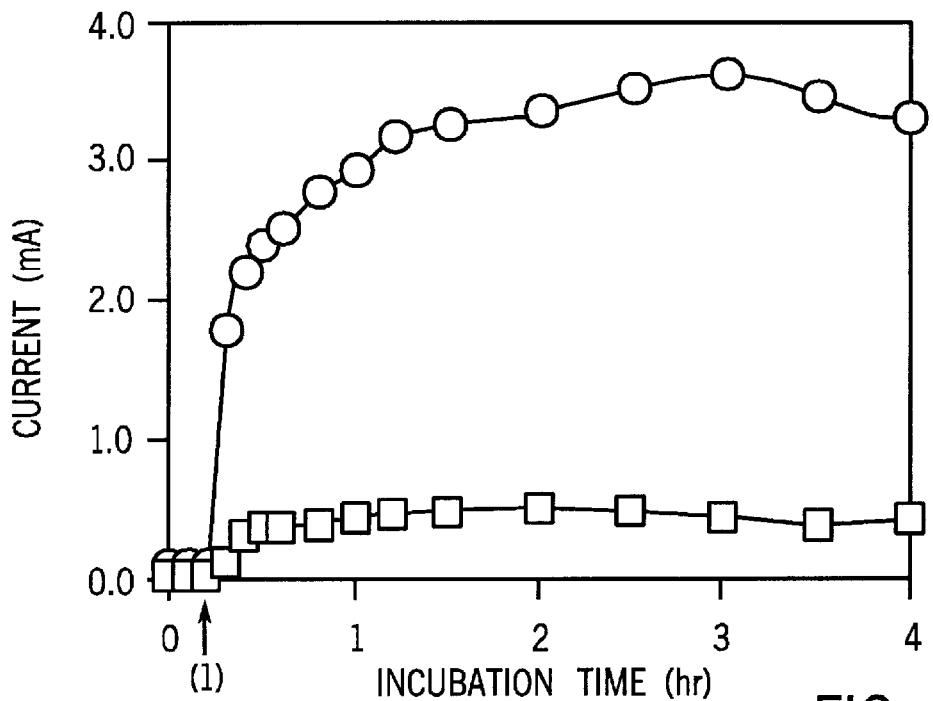
FIG. 4 shows the current and potential obtained in a glucose fuel cell using *E. coli* K-12 resting cells and neutral red or thionin.
Figure 4B:
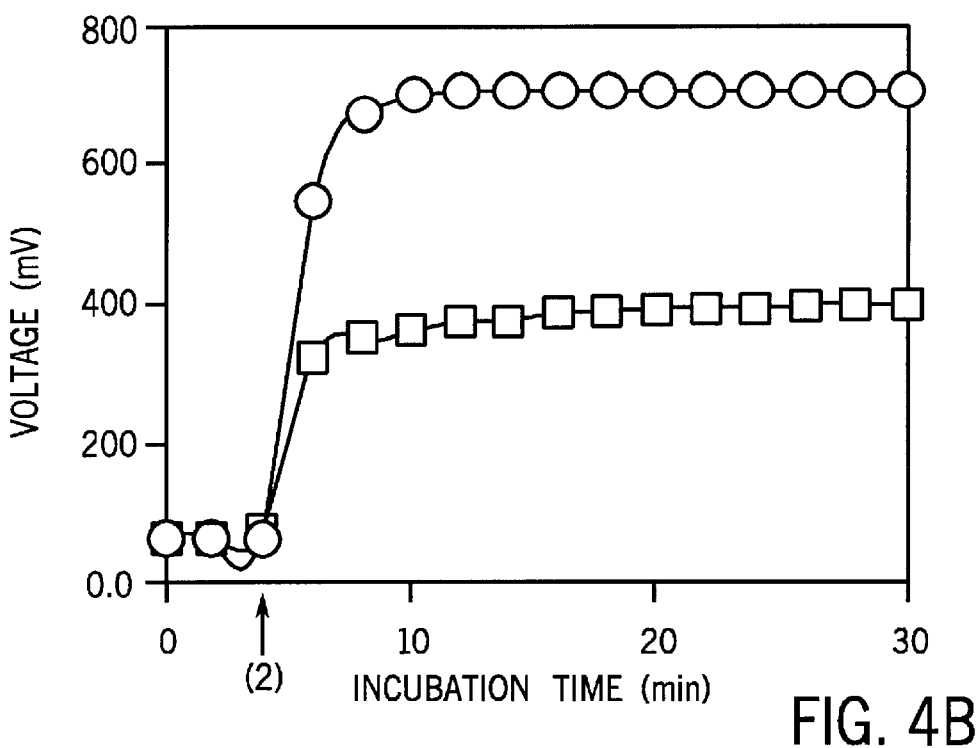

FIG. 4 compares the currents and potentials generated from glucose by E. coli resting cells in a glucose (10 g/L) fuel cell with either 100 μM NR (circles) or 300 μM thionin (squares) in closed circuit (current) (A) and open circuit (potential) (B) configurations. Arrows mark (1) the addition of the electron mediator; and (2) conversion to open circuit. Under the anaerobic conditions used, higher current and potential levels were produced with NR than with thionin as the electronophore. In control experiments under aerobic conditions, significant levels of current or potential were not detectable because NR and thionin cannot oxidize NADH through the electron transport system since $O_2$ is a much better electron acceptor (i.e., it has a much more positive $E_0'$ value than the two electron mediators). Under anaerobic conditions, E. coli normally couples NADH oxidation with reduction of either fumarate to succinate, acetyl CoA to ethanol, or pyruvate to lactate. These reactions are inhibited in the presence of NR in the fuel cell, and electricity is produced in lieu of these normal reduced metabolic end products.

Previous investigations (Allen, et al., 1993, Appl. Biochem. Biotechnol. 39–40:27–40 and Thurston, et al., 1985, J. Gen. Microbiol. 131:1393–1401) have shown in microbial fuel cells using thionin as the electron mediator, that both current and potential drop when the resting cells are depleted of glucose. We performed experiments to determine what maximal electrical productivities and stabilities can be generated by resting E. coli cells from different glucose concentrations in a fuel cell with NR as the electronophore.

Table 2 shows the effect of glucose concentration on the maximal electrical productivities and stabilities in an open circuit versus a closed circuit, with and without a 120 ohm external resistance. The maximal current, potential, and electrical energy produced by the fuel cell were proportional to the glucose (i.e., fuel) concentration. The maximum current and coulombic yields obtained from glucose using NR as the electronophore far exceeded those obtained with thionin in other investigations (Dealney, et al., 1984, Chem. Tech. Biotechnol. 34B:13–27).

Figure 5A:
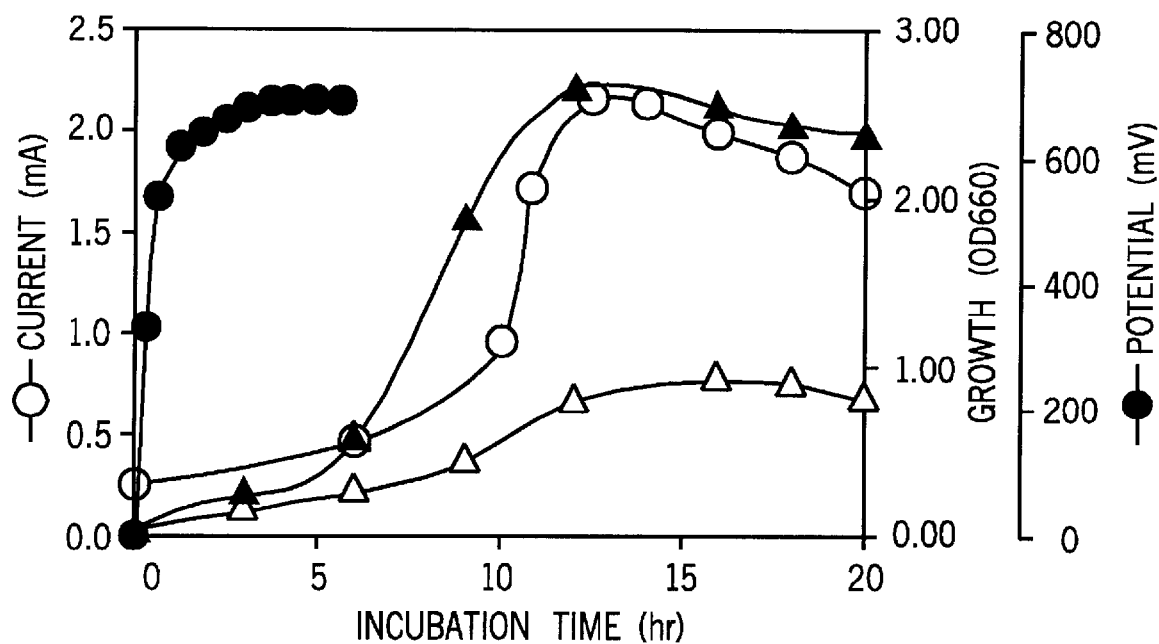
FIG. 5 shows the electrical current and potential levels obtained using *A. succinogenes* growing or resting cells.
Figure 5B:
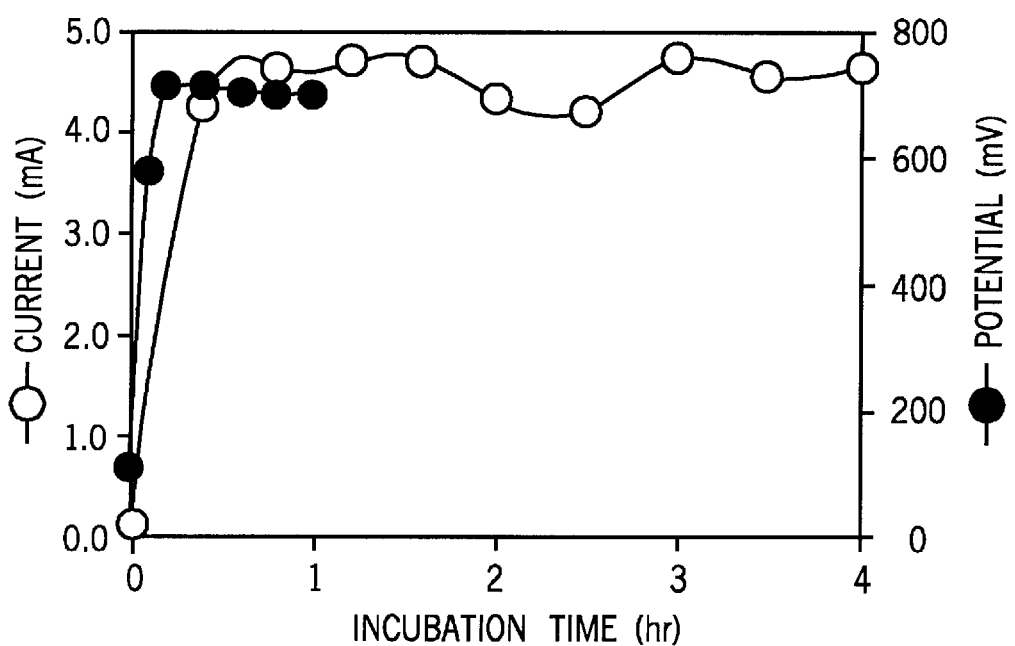

Previous studies (Roller, et al., 1984, J. Chem. Tech. Biotechnol. 34B:3–12 and Bennetto, et al., 1985, Biotechnol. Lett. 7:699–105) on microbial fuel cells with thionin as the electron mediator were only performed with resting cell suspensions (i.e., cells harvested after growth had ended). Using NR (100 μM) as the electronophore, we compared the electrical productivities (i.e., current and potential) of A. succinogenes growing cells (FIG. 5A) and resting cells (FIG. 5B) in a glucose (10 g/L) microbial fuel cell under anaerobic conditions (FIG. 5). Control experiments (FIG. 5A) showed that the growth yield and rate (squares) were much higher in the absence of NR when no electricity was generated (triangles) than in the presence of NR. The electric current (open circles) and potential (closed circles) generated increased with cell growth. The potentials generated by growing and resting cells were similar, whereas the current produced by resting cells was significantly higher (about 2-fold) than that produced by growing cells. The specific current produced per mg cell protein per hour was calculated at 10 hours for growing cells (1.235 mA/mg protein/hr) and at 2 hours for resting cells (2.595 mA/mg protein/hr) when the glucose levels were high. A total of 68 coulombs was produced by growing cells at 20 hours (after glucose was depleted); whereas the resting cells had produced 90 coulombs at 4 hours.

TABLE 2

Effect of initial glucose concentration on electrical productivity and stability of a microbial fuel cell using E. coli resting cells and NR as the electronophore.

| | Open Circuit | | Closed Circuit | | Closed Circuit with a 120Ω Resistance | | | | |
|---|---|---|---|---|---|---|---|---|---|
| Glucose (mM) | Potential (volt) | Current (mA) | Potential (volt) | Current (mA) | Potential (volt) | Current (mA) | Coulomb (amp/sec) | Electrical Energy (J) | Electrical Stability (hr) |
| 11.1 | 0.58 | 0.0 | 0.02 | 1.2 | 0.46 | 0.5 | 57.6 | 26.5 | 32 |
| 55.5 | 0.65 | 0.0 | 0.04 | 5.6 | 0.57 | 3.6 | 1049.76 | 598.4 | 81 |

TABLE 2-continued

Effect of initial glucose concentration on electrical productivity and stability of a microbial fuel cell using *E. coli* resting cells and NR as the electronophore.

| | Open Circuit | | Closed Circuit | | Closed Circuit with a 120Ω Resistance | | | | |
|---|---|---|---|---|---|---|---|---|---|
| Glucose (mM) | Potential (volt) | Current (mA) | Potential (volt) | Current (mA) | Potential (volt) | Current (mA) | Coulomb (amp/sec) | Electrical Energy (J) | Electrical Stability (hr) |
| 111 | 0.85 | 0.0 | 0.05 | 17.7 | 0.62 | 4.8 | 2039.04 | 1264.2 | 118 |

Similar experiments were performed using anaerobically grown *E. coli* cells in the presence or absence of electrical generation. Electrical generation dramatically decreases growth yield, ATP yield and metabolite production (Table 3). Table 4 compares substrate consumption, growth and electricity production by exponential versus stationary phase *E. coli* cells. These data indicate that significantly more electricity is produced by stationary phase cells than by exponential phase cells. This result was expected because significant reducing power is required for cell growth that cannot be directed to electricity generation.

TABLE 3

Comparison of anaerobic metabolism of *E. coli* during anaerobic growth in the presence or absence of electrical generation[a].

| Growth Condition | Glucose Consumption (mM) | Cell Mass (g/L) | Ysub (g cell/mol substrate) | Products (mM) | Theoretical ATP yield (mol/mol sub) | Electricity Energy (J/mol sub) |
|---|---|---|---|---|---|---|
| Without Electricity Generation | 60.6 | 3.07 | 50.12 | 11.93 | 7.07 | — |
| With Electricity Generation | 66.3 | 1.4088 | 22.082 | 8.88 | 2.57 | 1320.0 |

[a]Data was determined after 20 hours of growth in medium A with 100 μM neutral red in a standard fuel cell.

TABLE 4

Comparison of substrate consumption and electricity production by anaerobic *E. coli* exponential phase versus stationary phase cells in a fuel cell using neutral red as electronophore[a].

| Exponential Phase Cells | | | Stationary Phase Cells | | |
|---|---|---|---|---|---|
| Glucose Consumption | Cell Mass | Electricity Energy (J/mol sub) | Glucose Consumption | Cell Mass | Electricity Energy (J/mol sub) |
| 45.1 mM (7.52 mM/hr) | 1.74 g/L (0.29 g/L/hr) | 100.8 | 15.5 mM (2.59 mM/hr) | 0.214 g/L (0.035 g/L/hr) | 1207.7 |

[a]Data for exponential phase cells is from 0–6 hours after inoculation. Data for stationary phase cells is 12–18 hours after inoculation. Conditions: medium A with 100 μM neutral red in the standard fuel cell system.

Figure 6:
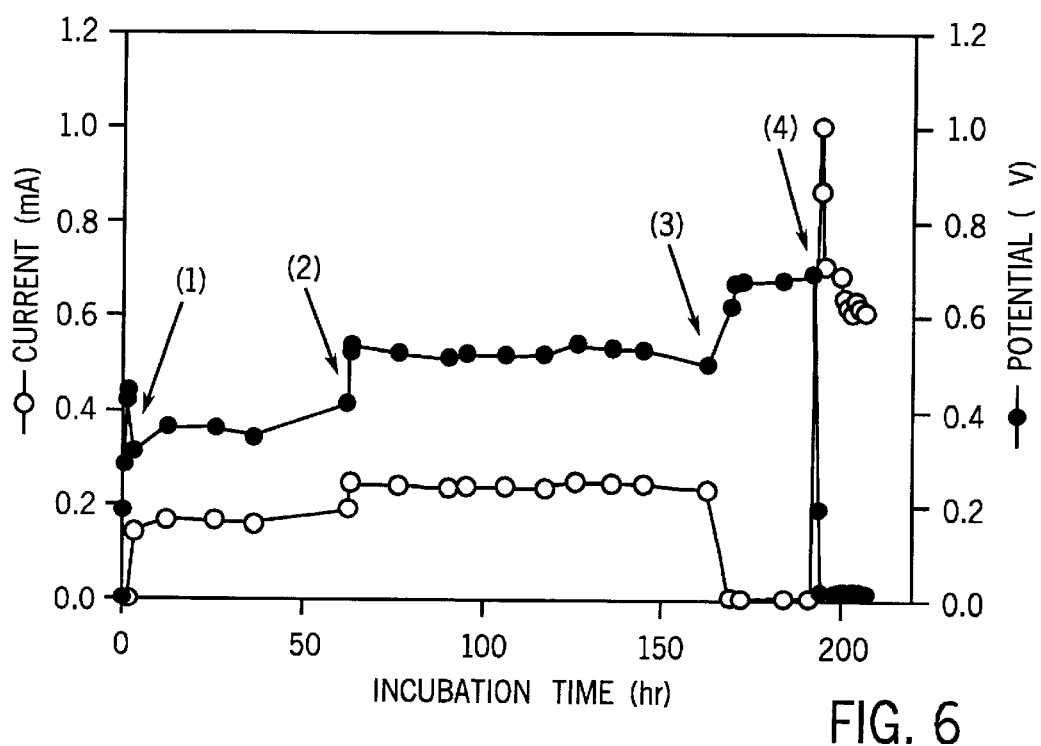
FIG. 6 shows the current and potential produced in a glucose (3 g/L) fuel cell using anaerobic sewage sludge as catalyst and NR (100 µM) as the electronophore.

Experiments were initiated using anaerobic sludge to test its potential as a catalyst for electricity generation in a fuel cell with NR as the electronophore. FIG. 6 shows the effect of glucose addition on the current and potential generated by the sewage sludge, as well as the maximum current produced in a closed circuit configuration versus the maximum potential produced in an open circuit configuration. The numbered arrows connote the conversion from open to closed circuit with a 2.2 kohms resistance (1); addition of 3 g/L glucose (2); conversion from closed to open circuit (3); and the conversion from open to closed circuit without external resistance (4). The electrical productivity of the glucose fuel cell using sewage sludge as the catalyst was calculated to be a total of 370.8 C (G of 162.82 J).

We have shown here that NR serves as a superior electronophore or electron mediator than thionin in microbial fuel cells using glucose as fuel. Furthermore, we have shown that resting cells generate more electricity than growing cells, and that mixed cultures such as sewage sludge can be robust catalysts for electricity generation in fuel cells utilizing NR as the electron mediator.

Figure 7A:
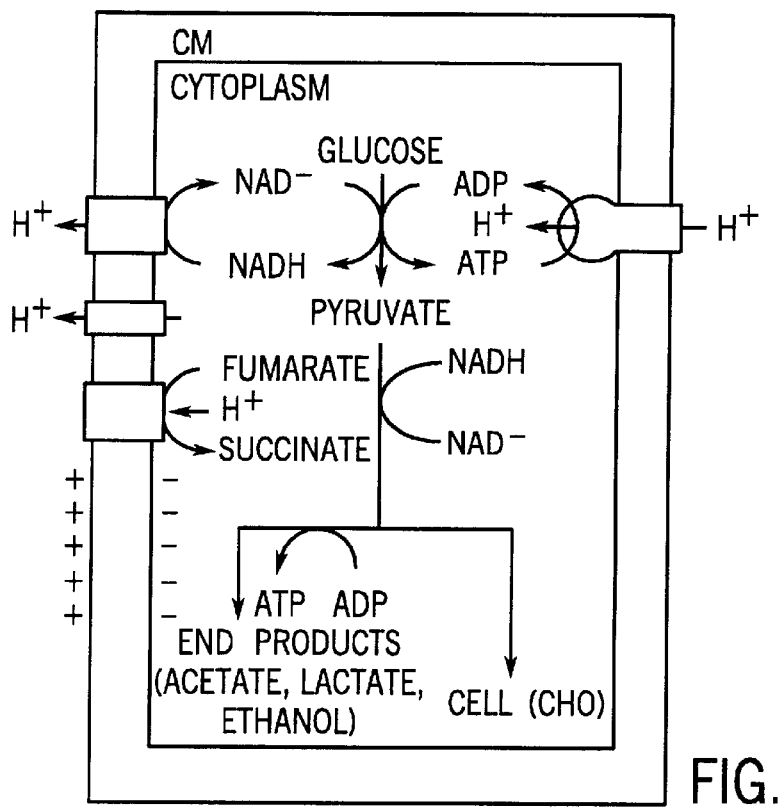
FIG. 7 is a proposed model of the energy flow in cells under normal (A) or electrogenic (B) glucose metabolism.
Figure 7B:
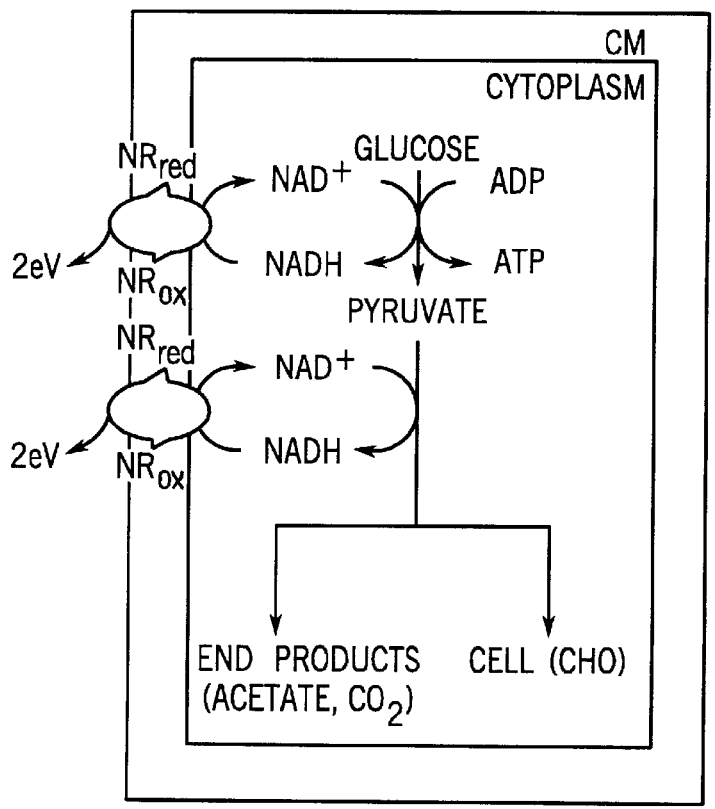
Figure 8:
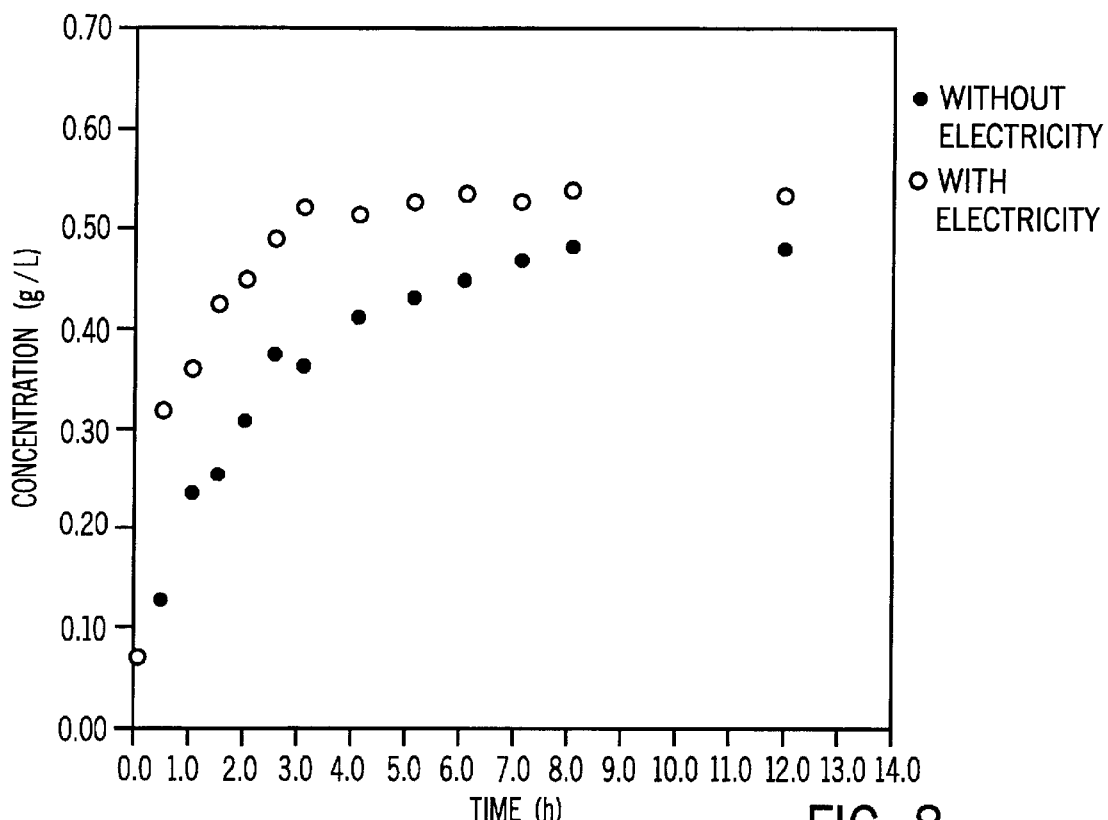
FIG. 8 is a time course for biotransformation of β-tetralone to β-tetralol by the yeast *T. capitacum* at 1 g/L of substrate in the presence and absence of 1.5 volt electricity.

FIG. 7 summarizes our working model explaining *E. coli* (or *A. succinogenes*) metabolic properties in fuel cells using NR as the electron mediator versus during normal (A) versus electrogenic glucose metabolism (B) of *E. coli* or *A. succi-*

*nogenes* in a fuel cell with NR as the electronophore. Cell growth, ATP synthesis, and reduced end product formation decrease in relation to the amount of electricity generated. In the presence of NR, cell growth is significantly reduced and NADH is oxidized via NR-mediated electrical generation in lieu of producing normal reduced end products (i.e., succinate, lactate, and ethanol). Cells still generate ATP by substrate-level phosphorylation (i.e., acetate kinase) but grow slower because they cannot generate ATP by electron transport-mediated phosphorylation (i.e., fumarate reductase).

NR is superior to thionin as an electron mediator because it enhances both the rate of electron transfer (current) and the yield of electrons transferred (coulombic yield). The highest current (>17 mA) produced in a microbial fuel cell using NR was significantly higher than that achieved previously with thionin as the electron mediator (Roller, et al., 1984, *J. Chem. Tech. Biotechnol.* 34B:3–12 and Allen, et al., 1993, *Appl. Biochem. Biotechnol.* 39–40:27–40); it is, however, still low in electrical terms. There may be potential applications for low-power DC microbial fuel cells such as to maintain telecommunications in remote areas including outer space.

Example 2

Bioreduction of Ketones to Alcohols

Introduction

Bioreductions of ketones require either NADH or NADPH as a co-factor and the difficulty in implementing an efficient and economical recycling system has restricted large scale applications to whole cell processes. Specifically, we are interested in asymmetric bioreduction of a β-tetralone to its corresponding (S)-alcohol by the yeast *Trichosporon capitatum*. The alcohol, β-tetralol, is subsequently used in the synthesis of MK-0499, a very potent potassium channel blocker which mediates polarization of cardiac tissues.

Recently, we have developed an electrochemical co-factor recycling technology using an electrochemical bioreactor system (described above). The technology was examined and demonstrated in fermentation processes producing organic acids and in reducing $CO_2$ to $CH_4$ with an activated sludge, resulting in a 20–40% increase in the end product concentration.

We have evaluated the electrochemical co-factor (NAD) recycling technology using either whole cells of *Trichosporon capitatum* (strain MY 1890) or an oxidoreductase isolated from this organism, to support the bioreduction of 6-bromo-β-tetralone (L735, 707) to its corresponding alcohol 6-bromo-β-tetralol. In this Example, we present the data on increased biotransformation rate and β-tetralol concentration using this new electrochemical co-factor technology.

Materials and Methods

Electrochemical Bioreactor System

An electrochemical bioreactor (ECB) was designed and constructed to conduct biotransformation in the presence and absence of an electrically reduced system. The ECB was separated into anode and cathode compartments by a cation selective membrane septum (φ 22 mm, Nafion, Electrosynthesis, NY). The anode and cathode electrodes were made from graphite fine woven felt (6 mm thickness, 0.47 $m^2g^{-1}$ of available surface area, Electrosynthesis, NY). The weights of the electrodes were adjusted to 0.5 g (10×50 mm). The voltage and current between the anode and cathode were measured using a precision multimeter, and were adjusted to 0.7–10.0 volt and 0.5–10 mA, respectively.

The total volume of each compartment was 70 mL with a working volume of 40 mL. The reaction mixture was placed in the cathode compartment, whereas 100 mM phosphate buffered saline was filled in the anode compartment.

Microorganism and Medium Composition

*Trichosporon capitatum* MY 1890 (received from the Merck & Co.) was grown on culture medium containing glycerol, 30 g/L; soytone, 25 g/L and yeast extract, 10 g/L. The culture was grown in 200 mL medium in a 1 L baffled flask and was incubated on a 200 rpm orbital shaker at 29–30° C. for 48 hours.

Preparation of Biomass for Biotransformation

The cells from a 48 hour grown culture were harvested by centrifugation at 8000 rpm for 30 minutes. The cell pellet was resuspended in the same volume (200 ml) of 50 mM Tris buffer (pH 7.0), and washed twice with the buffer by centrifugation.

Biotransformation with Biomass

The washed cells were resuspended in 50 mM Tris buffer (pH 7.0) in an appropriate volume to achieve 1×, 2× and 3× biomass concentration. The reaction mixture contained cell suspension, β-bromo-tetralone, ethanol, 100 nM neutral red and 50 mM Tris buffer (pH 7.0). Biotransformation was conducted in the ECB system on a reciprocal shaking incubator (200 strokes/min) at 30° C.

Analysis of Substrate and Product

β-Bromo-tetralone and β-bromo-tetranol were analyzed by a Waters HPLC 640 equipped with a Zorbax RX-C8 column. The absorbency was measured at 220 nm. The mobile phase containing 50% acetonitrile and 50% acidified water (0.1% phosphoric acid) mixture was used at a flow rate of 1.0 ml/L.

Results and Discussions

Figure 9:
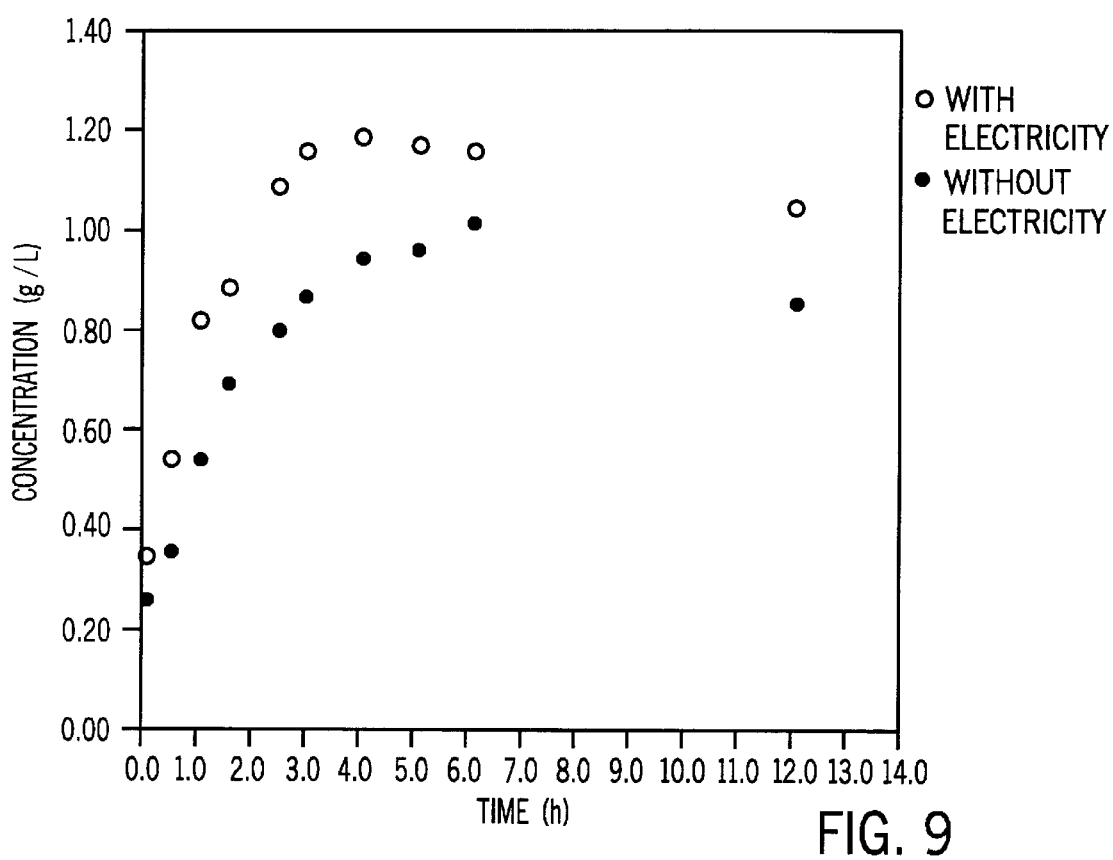
FIG. 9 is a time course of biotransformation of β-tetralone to β-tetralol by the yeast *T. capitacum* at 2 g/L of substrate in the presence and absence of 1.5 volt electricity.

Biotransformation of β-tetralone to β-tetralol with a 48 Hour *Trichosporon canitatum* Culture in the Presence of 1.5 Volt Electricity Comparison of the biotransformation in the presence of 1.5 volt to the absence of electricity was carried out with 1 g/L of substrate in the electrochemical bioreactor system. As shown in FIG. 9, the rate of β-tetralol formation in the presence of the electricity was significantly higher than without the electricity. The overall reaction rate during the first 3 hour reaction was increased by 45%. Although the reaction rate gradually decreased, the high initial reaction rate resulted in a faster completion of the biotransformation. In the presence of the electricity the product formation was completed in 3 hours. However, in the absence of the electricity, the reaction was prolonged up to 8 hours and the final end product concentration was lower than what was achieved with the electricity (0.53 g/L). It is important to note the high initial reaction rate was observed within the first hour in the presence of electricity.

Biotransformation of β-tetralone at 2 g/L of Substrate

Figure 10:
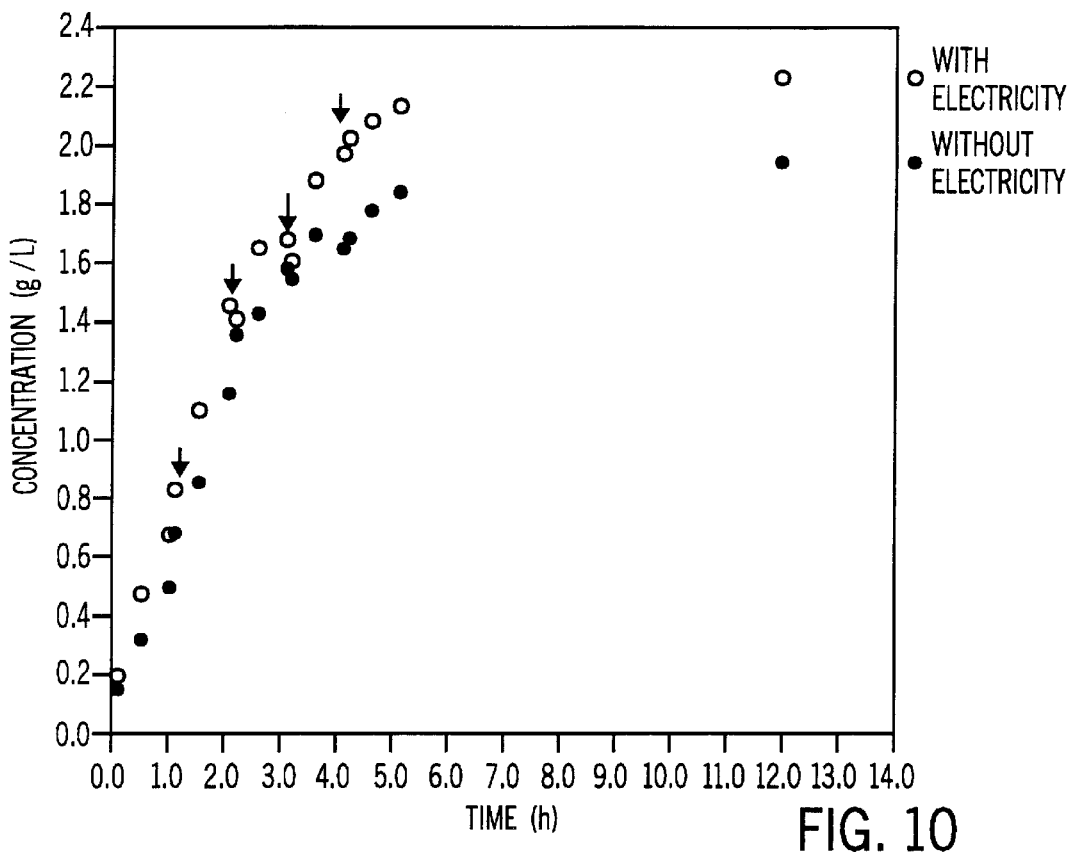
FIG. 10 is the effect of pulse feeding of 2 g/L of substrate on the biotransformation of β-tetralone to β-tetralol.

Assuming that the biotransformation yield was limited by the availability of the substrate, the level of substrate was increased to 2 g/L while maintaining 1.5 volt of electricity. The product concentration increased to 1.2 g/L in about 3–4 hours (FIG. 10). This product concentration correlates well with 0.53 g/L at 1 g/L of substrate in nearly the same reaction time. The initial reaction rate was also dramatic in this experiment (2 g/L substrate). Based on these results, it was decided to maintain 2 g/L substrate level to achieve higher levels of reaction rates and the end product.

Biotransformation with Pulse Feeding of Substrate

Figure 11:
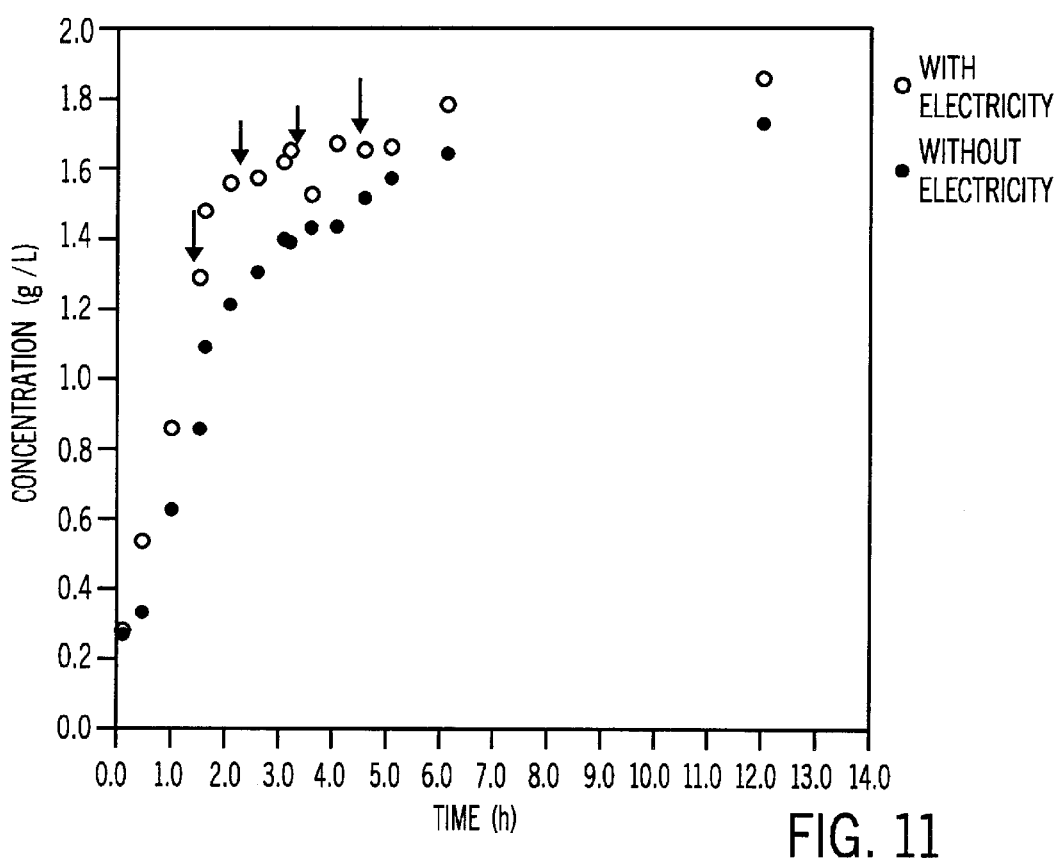
FIG. 11 is the effect of pulse feeding of 1 g/L of substrate on the biotransformation of β-tetralone to β-tetralol.
Figure 12:
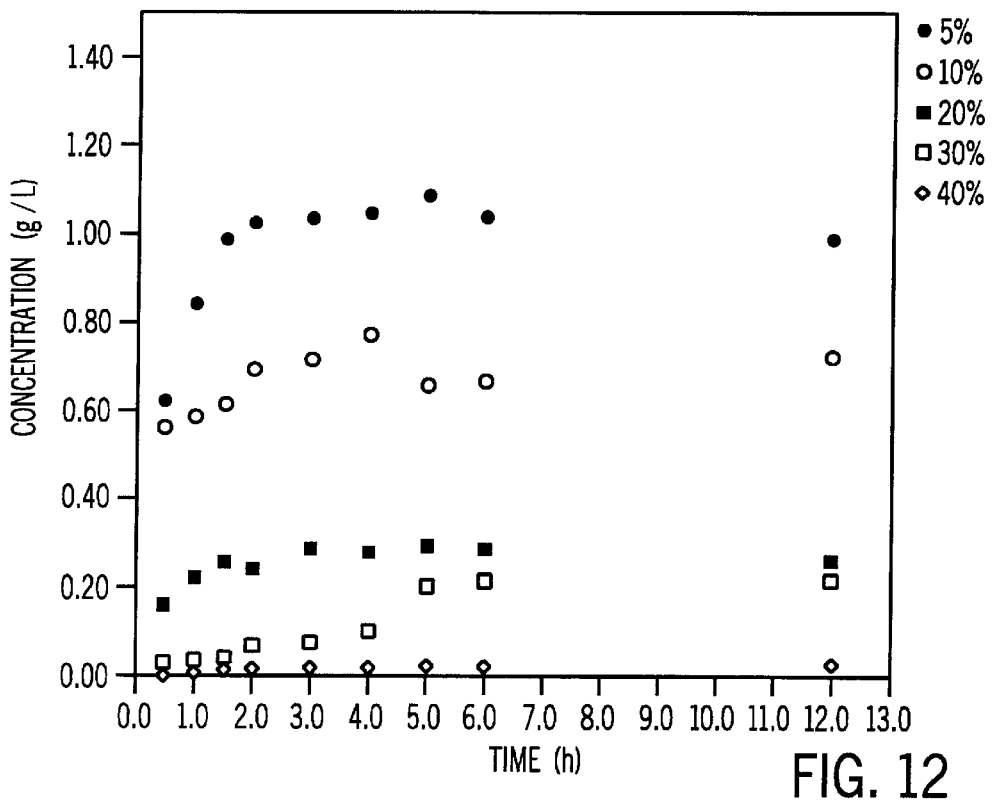
FIG. 12 is the effect of ethanol concentration on the biotransformation of β-tetralone to β-tetralol.

To maintain the higher substrate concentration in the reaction mixture, pulse feeding of 2 g/L of substrate was done at 1.5–2 hour interval for a total of 4 times. Although pulse feeding of the substrate was followed by an increase in product formation up to 2.2. g/L in the presence of electricity (FIG. 11), this increase was not in proportion to the amount of total fed substrate. Because the substrate β-tetralone has a very low solubility in the aqueous phase, a larger part of the substrate remained in the insoluble form, and some of it was probably also adsorbed onto the graphite felt of the electrode. Thus, only limited substrate was converted to the end product. To reduce the unutilized substrate, the concentration of the substrate pulse fed to the reaction mixture was reduced to 1 g/L. The results indicate that although product concentration decreased from 2.2 g/L (at 2 g/L substrate) to 1.8 g/L at 1 g/L substrate (pulse feeding), there was almost no change in the reaction rate when the substrate was pulse fed at 1 g/L (FIG. 12).

Effect of Ethanol Concentration on the Biotransformation

Figure 13:
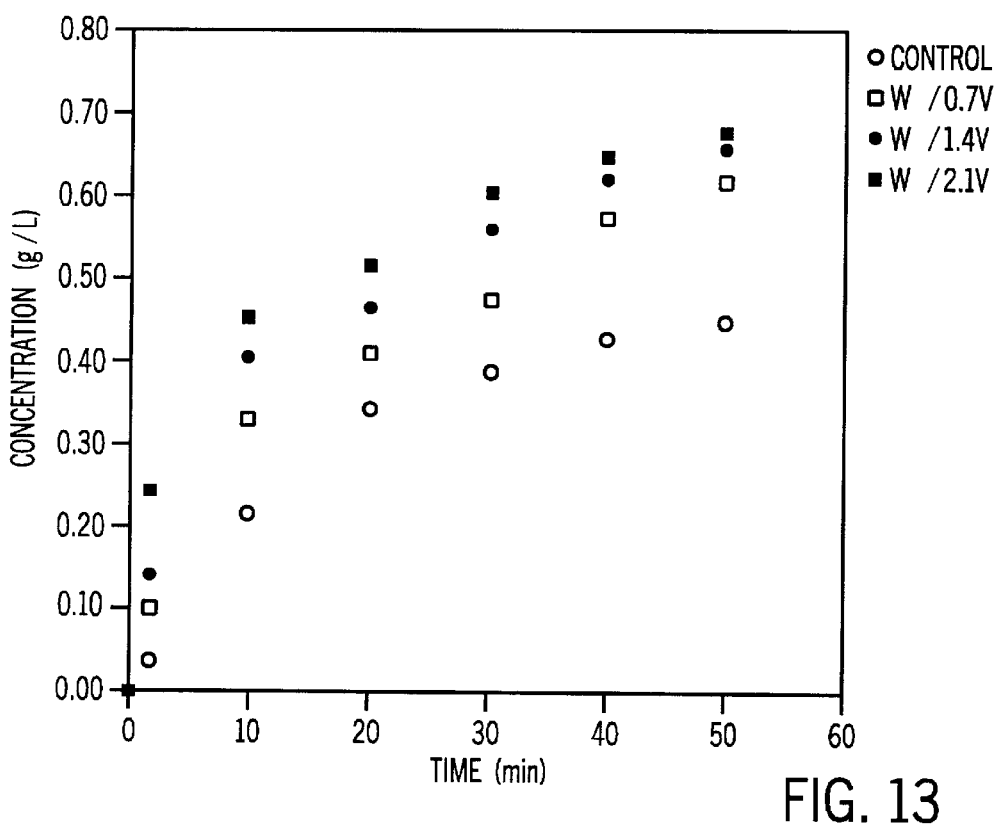
FIG. 13 is the effect of electrical potential on the biotransformation of β-tetralone to β-tetralol.

Since the substrate was poorly soluble in water, it was dissolved in 5% ethanol. Assuming that a higher dissolved substrate might result in increased end-product concentration in the ECB system, ethanol concentration was increased from 5 to 50% to increase the amount of soluble substrate. As the results presented in FIG. 13, the increased ethanol concentration adversely affected the reaction rate and resulted in a low final product formation presumably due to ethanol toxicity. The highest reaction rate as well as the product concentration was achieved with 5% ethanol. Thus, another method has to be applied to increase the solubility of the substrate to test the hypothesis that a higher dissolved substrate will result in high biotransformation rates and product yields.

Effect of Various Levels of Electricity on Biotransformation Rate

Since the biochemical reactions are affected by the amount of available reducing power, we examined the effect of various levels of electricity on the rate of the biotransformation of β-tetralone to β-tetralol. In the first experiment, 0, 0.7, 1.4 and 2.1 volt of electricity was supplied. In the second experiment, the electricity was increased up to 10 volt. For these two experiments, two different batches were used. As shown in FIGS. 6(1) and 6(2), electricity up to 5 volts enhanced the reaction rate and the final product concentration. It seems that a higher electric supply provides a higher driving force for the reductive reaction. However, the reaction rate was drastically affected within 20 minutes with 10 volts of electricity. It is likely that the high electrical potential of 10 volts caused the denaturation of protein, thus affected the cellular metabolic reactions. The initial reaction rate with different levels of electricity are presented in Table 5. The results demonstrate that the electricity enhanced the reaction rate, e.g. with 5 volts electricity, the biotransformation rate increased to two-fold in comparison to the rate without the electricity.

TABLE 5

Relationship between electrical potential and the biotransformation rate

| | Reaction rate (mg/L/min) in 20 minutes | |
|---|---|---|
| Voltage | 1st trial | 2nd trial |
| 0 (control) | 17.0 | 14 |
| 0.7 | 21.0 | — |
| 1.4 | 23.0 | — |
| 2.1 | 26.0 | 21.5 |
| 3.5 | — | 24.5 |
| 5.0 | — | 26.9 |
| 10.0 | — | 12.6 |

Biotransformation with Variable Biomass, Voltage and Substrate in a Matrix Design Our results have demonstrated a high initial rate of biotransformation of β-tetralone to β-tetralol in the ECB system. We have also observed an electricity-dependent increase in the reaction rate as well as a substrate concentration-dependent increase in the β-tetralol concentration. However, these experiments do not explain the cumulative effect of the electricity, substrate concentration and the amount of biomass on the reaction rate.

Therefore, to examine the combined effect of biomass, electricity and substrate on the biotransformation of β-tetralone, we conducted experiments according to a "BB matrix design 6" provided by Merck & Co. Initial reaction rates were determined within 10 minutes and these measurements were accomplished by using 4 different batches of the culture with internal controls. Comparison of the initial reaction rates at different substrate concentrations shows that the specific reaction rates were significantly affected by the electricity and biomass at higher substrate concentration (up to 4 g/L), but not at 1 g/L (Table 6). Similarly, a higher electricity (6 volt) resulted in a high specific reaction rate (8.1 mg/L/min/g) at a moderate level of biomass and high substrate concentration or vice versa. A similar reaction rate was also achieved by a moderate level of electricity (3.5 volt), but under high biomass (3×) and substrate (4 g/L) conditions. Our results also show that low biomass concentrations resulted in a significantly enhanced specific reaction rate (6.46 mg/L/min/g) by provide high electricity. However, an increased biomass (2×) was necessary to obtain the similar reaction rate (6.54 mg/L/min/g) if electricity was reduced from 6.0 to 3.5 volt (Table 6).

TABLE 6

Cumulative effect of biomass, voltage and substrate on the initial specific reaction rate in a BB Matrix Design 6.

| Biomass | Voltage | Substrate Conc. (g/L) | Initial reaction rate (mg/L/min) | Specific reaction rate (mg/L/min) |
|---|---|---|---|---|
| Culture batch #1: Dry weight of biomass: 10.23 g/L | | | | |
| 1.0 | 3.5 | 1.0 | 24.6 | 2.40 |
| 2.0 | 3.5 | 2.5 | 46.7 | 4.57 |
| 2.0 | 1.0 | 4.0 | 56.4 | 5.52 |
| 3.0 | 3.5 | 2.5 | 66.9 | 6.54 |
| 0.0 | 0.0 | 2.5 | 0.0 | 0 |
| 1.0 | 3.5 | 4.0 | 48.3 | 4.72 |
| 1.0 | 1.0 | 2.5 | 29.8 | 2.91 |
| 2.0 | 0.0 | 2.5 | 31.2 | 3.05 |
| Culture batch #2: Dry weight of biomass: 7.31 g/L | | | | |
| 1.0 | 3.5 | 4.0 | 59.6 | 8.15 |
| 1.0 | 6.0 | 2.5 | 47.2 | 6.46 |
| 2.0 | 3.5 | 2.5 | 32.8 | 4.49 |
| 2.0 | 6.0 | 4.0 | 59.7 | 8.17 |
| Culture batch #3: Dry weight of biomass: 7.21 g/L | | | | |
| 3.0 | 1.0 | 2.5 | 44.0 | 6.10 |
| 2.0 | 1.0 | 1.0 | 20.2 | 2.80 |
| 3.0 | 6.0 | 2.5 | 58.7 | 8.14 |
| 2.0 | 6.0 | 1.0 | 26.8 | 3.72 |
| Culture batch #4: Dry weight of biomass: 8.20 g/L | | | | |
| 3.0 | 3.5 | 1.0 | 33.5 | 4.08 |
| 2.0 | 6.0 | 4.0 | 73.4 | 7.98 |
| 2.0 | 3.5 | 2.5 | 37.4 | 4.56 |
| 1.0 | 0.0 | 2.5 | 19.5 | 2.38 |

Biotransformation with Purified β-Tetralone Reductase

Figure 14:
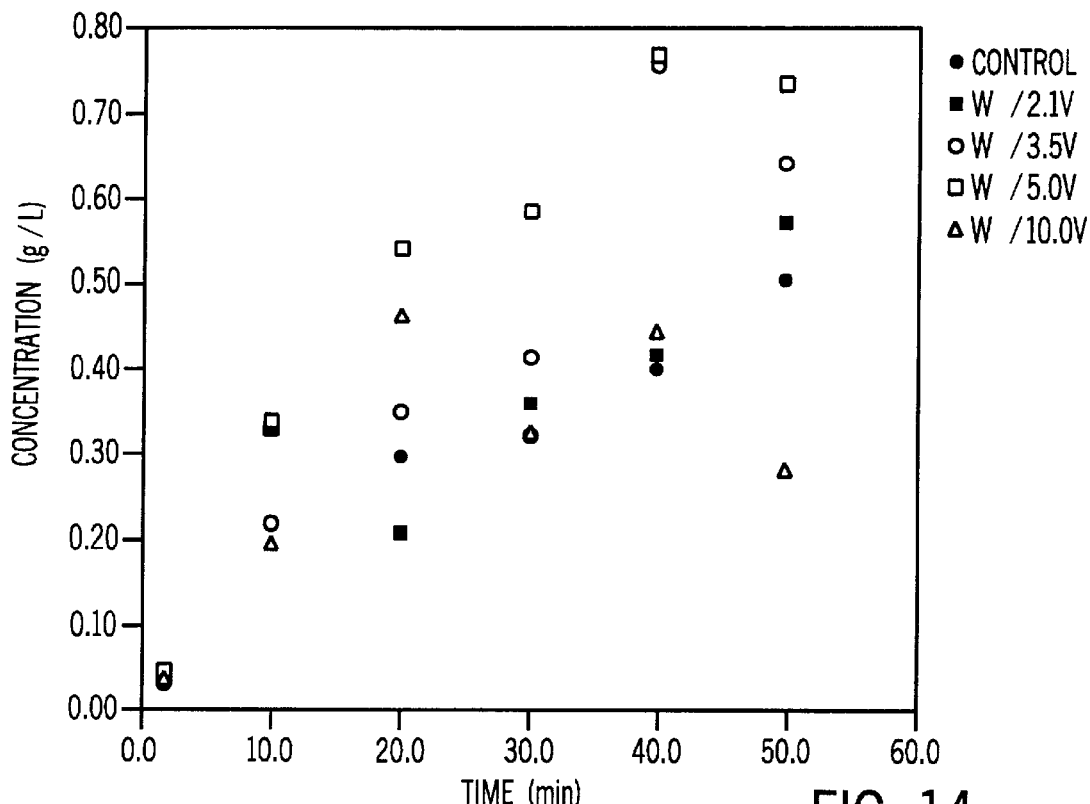
FIG. 14 is the effect of electrical potential on the biotransformation of β-tetralone to β-tetralol.
Figure 15:
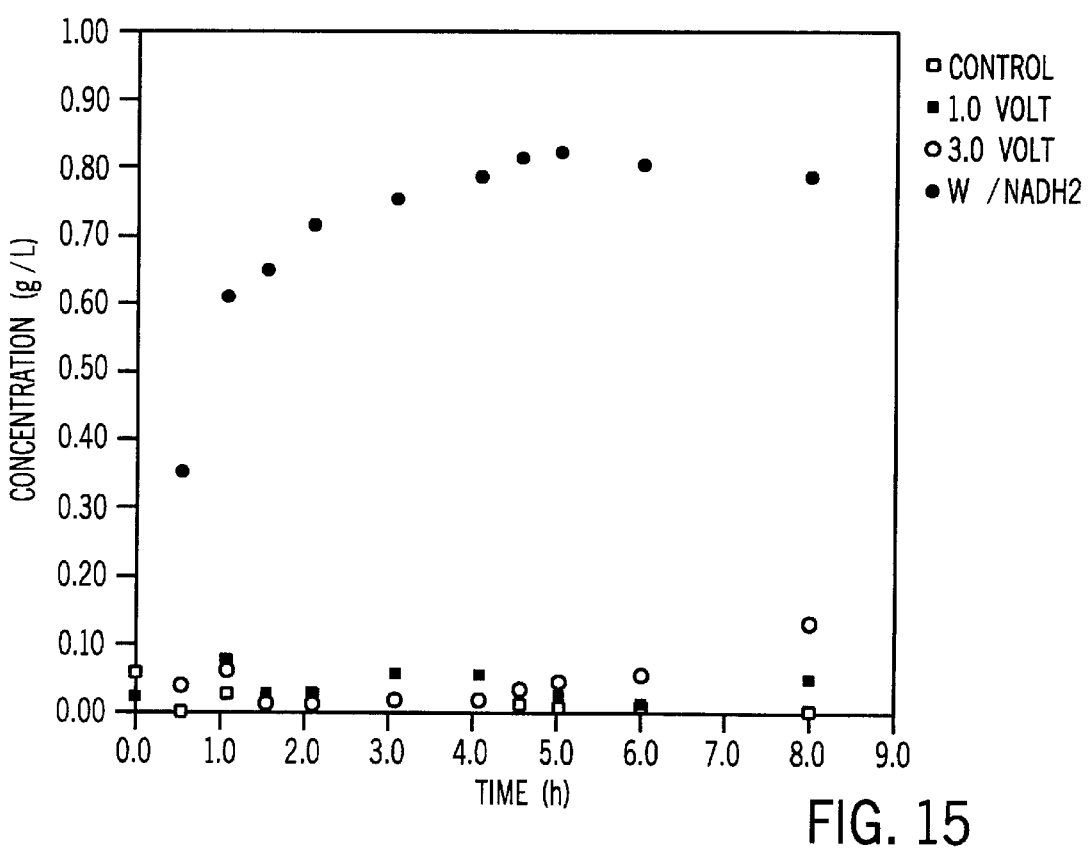
FIG. 15 is the biotransformation kinetics with purified β-tetralone reductase with NAD in the presence of electricity.

Enzymatic biotransformation was conducted with 0.02 unit/ml of the purified β-tetralone reductase, 10 mM NAD and 10 mM β-tetralone in the presence of 0, 1.0 and 3.0 volt of electricity. To confirm the enzyme reaction, one reaction mixture was prepared as a control with NADH$_2$ instead of NAD, in the absence of electricity. The results show that 0.13 g/L of the product was produced with 3 volt of electricity after 8 hour incubation, whereas only a trace amount of the product was found in the reaction mixture with 0 and 1.5 volt of electricity (FIG. 14). In comparison, about 0.8 g/L of the product was produced with NADH$_2$. It is not clear why the enzymatic reaction rate with 3 volt electricity was slow.

Conclusion

In this study, it was demonstrated that the initial rate of biotransformation of β-tetralone to β-tetralol and the final product concentration were enhanced due to electricity-based reducing power in the electrochemical bioreactor system. It was found that the biotransformation rate was significantly affected by the amount of biomass, substrate concentration and electrical potential. The influence of electrical potential on the biotransformation rates was more significantly observed at a high substrate level of 2.5–4 g/L. The ECB system has shown a great potential in reducing the reaction time that is likely to result in significant cost savings.

The present invention is not limited to the exemplified embodiments, but is intended to encompass all such modifications and variations as come within the scope of the following claims.

We claim:

1. A method of promoting reductive processes in a biological system comprising the steps of:
   (a) providing an electrochemical bioreactor system having a cathode compartment equipped with a cathode and an anode compartment equipped with an anode, the cathode and anode compartment being separated by a cation selective membrane, wherein the cathode and anode are connected by a conductive material to a power supply;
   (b) placing a suitable amount of neutral red and a biological catalyst in the cathode compartment; and
   (c) applying from the power supply a current between the anode and the cathode wherein at least a portion of the neutral red is electrically reduced,
wherein the biological catalyst comprises *Trichosporon capitatum*.

2. The method of claim 1, wherein the cathode compartment comprises a ketone or aldehyde substrate.

3. The method of claim 2, wherein the substrate is converted to a reduced product at a high rate, relative to the rate of product formation in a comparable system lacking neutral red.

4. The method of claim 2, wherein the substrate is converted to an alcohol.

5. The method of claim 4, wherein the substrate is 6-bromo-β-tetralone.

6. The method of claim 5, wherein the substrate is converted to 6-bromo-β-tetralol.

7. A method of promoting reductive processes in a biological system comprising the steps of:
   (a) providing an electrochemical bioreactor system having a cathode compartment equipped with a cathode and an anode compartment equipped with an anode, the cathode and anode compartment being separated by a cation selective membrane, wherein the cathode and anode are connected by a conductive material to a power supply;
   (b) placing a suitable amount of neutral red, NAD(H) or NADP(H), and a biological catalyst in the cathode compartment; and
   (c) applying from the power supply a current between the anode and the cathode wherein at least a portion of the neutral red is electrically reduced,
wherein the biological catalyst comprises a β-tetralone reductase.

8. The method of claim 7, wherein the cathode compartment comprises a ketone or aldehyde substrate.

9. The method of claim 8, wherein the substrate is converted to a reduced product at a high rate, relative to the rate of product formation in a comparable system lacking neutral red.

10. The method of claim 8, wherein the substrate is converted to an alcohol.

11. The method of claim 10, wherein the substrate is 6-bromo-β-tetralone.

12. The method of claim 11, wherein the substrate is converted to 6-bromo-βtetralol.

13. A method of promoting reductive processes in a biological system comprising the steps of:
   (a) providing an electrochemical bioreactor system having a cathode compartment equipped with a cathode and an anode compartment equipped with an anode, the cathode and anode compartment being separated by a cation selective membrane, wherein the cathode and anode are connected by a conductive material to a power supply;
   (b) placing a suitable amount of neutral red, 6-bromo-β-tetralone, and a biological catalyst in the cathode compartment; and
   (c) applying from the power supply a current between the anode and the cathode wherein at least a portion of the neutral red is electrically reduced.

14. The method of claim 13, wherein the biological catalyst comprises *Trichosporon capitatum*.

15. The method of claim 13, wherein the biological catalyst comprises a β-tetralone reductase.

16. The method of claim 13, wherein the 6-bromo-β-tetralone is converted to a reduced product at a high rate, relative to the rate of product formation in a comparable system lacking neutral red.

17. The method of claim 13, wherein the 6-bromo-β-tetralone is converted to an alcohol.

18. The method of claim 13, wherein the 6-bromo-β-tetralone is converted to 6-bromo-β-tetralol.

* * * * *

UNITED STATES PATENT AND TRADEMARK OFFICE
CERTIFICATE OF CORRECTION

PATENT NO. : 6,495,023 B1
DATED : December 17, 2002
INVENTOR(S) : Zeikus et al.

It is certified that error appears in the above-identified patent and that said Letters Patent is hereby corrected as shown below:

Column 28,
Line 27, delete "6-bromo-ßtetralol" and insert therefor -- 6-bromo-ß-tetralol --.

Signed and Sealed this

Fifth Day of August, 2003

JAMES E. ROGAN
*Director of the United States Patent and Trademark Office*